US012637679B2

(12) United States Patent
Spiess et al.

(10) Patent No.: US 12,637,679 B2
(45) Date of Patent: May 26, 2026

(54) APTAMER BASED SYSTEM TO QUANTIFY ANTI-THROMBIN III IN BLOOD

(71) Applicant: University of Florida Research Foundation, Incorporated, Gainesville, FL (US)

(72) Inventors: Bruce Davis Spiess, Gainesville, FL (US); Weihong Tan, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1077 days.

(21) Appl. No.: 17/767,349

(22) PCT Filed: Oct. 14, 2020

(86) PCT No.: PCT/US2020/055484
§ 371 (c)(1),
(2) Date: Apr. 7, 2022

(87) PCT Pub. No.: WO2021/076557
PCT Pub. Date: Apr. 22, 2021

(65) Prior Publication Data
US 2022/0372485 A1 Nov. 24, 2022

Related U.S. Application Data

(60) Provisional application No. 62/915,107, filed on Oct. 15, 2019.

(51) Int. Cl.
| | |
|---|---|
| *C12N 15/115* | (2010.01) |
| *C12Q 1/56* | (2006.01) |
| *C12Q 1/6818* | (2018.01) |
| *G01N 33/86* | (2006.01) |

(52) U.S. Cl.
CPC .............. *C12N 15/115* (2013.01); *C12Q 1/56* (2013.01); *C12Q 1/6818* (2013.01); *G01N 33/86* (2013.01); *C12N 2310/16* (2013.01); *C12N 2310/3517* (2013.01); *C12Q 2563/107* (2013.01); *G01N 2333/8128* (2013.01)

(58) Field of Classification Search
None
See application file for complete search history.

(56) References Cited

U.S. PATENT DOCUMENTS

| | | | |
|---|---|---|---|
| 5,319,072 | A | 6/1994 | Uemura et al. |
| 2003/0229213 | A1 | 12/2003 | Farrenburg et al. |
| 2009/0215125 | A1 | 8/2009 | Reed et al. |
| 2009/0311675 | A1 | 12/2009 | Hosokawa |
| 2010/0227320 | A1 | 9/2010 | Fu |
| 2013/0040837 | A1 | 2/2013 | Karp et al. |
| 2014/0255423 | A1 | 9/2014 | Hickman et al. |
| 2015/0064696 | A1 | 3/2015 | Takoh |

| | | | |
|---|---|---|---|
| 2019/0062688 | A1 | 2/2019 | Simonyi et al. |
| 2019/0135949 | A1 | 5/2019 | Cool et al. |
| 2025/0076264 | A1 | 3/2025 | Veige et al. |

FOREIGN PATENT DOCUMENTS

| | | |
|---|---|---|
| CN | 106693443 A | 5/2017 |
| WO | WO-2003/003988 A2 | 1/2003 |
| WO | WO-2005/059509 A2 | 6/2005 |
| WO | WO 2012/160033 A1 | 11/2012 |
| WO | WO 2021/076557 A1 | 4/2021 |

OTHER PUBLICATIONS

Extended European Search Report for European Application No. 20876697.2, dated Dec. 14, 2023, (14 pages), European Patent Office, Munich, Germany.

Li, Jingjing et al. "Binding-Induced Fluorescence Turn-On Assay Using Aptamer-Functionalized Silver Nanocluster DNA Probes", *Analytical Chemistry*, vol. 84, No. 12, May 18, 2012, pp. 5170-5174, DOI:10.1021/ac300626.

Li, Jingjing et al. "Supporting Information" for Jingjing Li et al., *Analytical Chemistry*, May 15, 2012, pp. S1-S8, available online: https://pubs.acs.org/doi/10.1021/ac3006268.

Tan, Ling et al. "Bivalent Ligands with Long Nanometer-Scale Flexible Linkers", *Biochemistry*, vol. 48, No. 2, Jan. 20, 2009, pp. 264-275, DOI: 10.1021/BI801630B.

Zehui, Cao et al. "Molecular Aptamers for Real-Time Protein-Protein Interaction Study", *Chemistry—A European Journal*, vol. 11, No. 15, May 13, 2005, pp. 4502-4508, DOI: 10.1002/CHEM. 200400983.

Xingfen, Liu et al. "Target-Induced Conjunction of Split Aptamer Fragments and Assembly with a Water-Soluble Conjugated Polymer for Improved Protein Detection", *Applied Materials & Interfaces*, vol. 6, No. 5, Feb. 27, 2014, pp. 3406-3412, DOI: 10.1021/ am405550j.

Li, Ye et al. "Thioflavin T as a Fluorescence Light-Up Probe for Both Parallel and Antiparallel G-Quadruplexes of 29-mer Thrombin Binding Aptamer", *Analytical and Bioanalytical Chemistry*, vol. 408, No. 28, Sep. 2, 2016, pp. 8025-8036, DOI: 10.1007/S00216-016-9901-5.

International Searching Authority, International Search Report and Written Opinion for International Application No. PCT/US2020/ 055484, dated Mar. 22, 2021, (17 pages), United States Patent and Trademark Office, USA.

Platella, Chiara et al. "G-Quadruplex-Based Aptamers Against Protein Targets in Therapy and Diagnostics," *Biochimica et Biophysica Acta*, vol. 1861, No. 5, (2017), (Published Online: Nov. 16, 2016), pp. 1429-1447, DOI: 10.1016/j.bbagen.2016.22.027.

(Continued)

*Primary Examiner* — Sean McGarry
(74) *Attorney, Agent, or Firm* — Alston & Bird LLP

(57) ABSTRACT

Compounds and compositions for determining the level of antithrombin (ATIII) in a sample are described. Methods of forming the compounds and compositions are also described. Methods of using the compounds and compositions to quantify the level of ATIII in a subject are further described. The methods can be used to facilitate determining a dosage or heparin or ATIII to administer to a patient.

18 Claims, 17 Drawing Sheets

Specification includes a Sequence Listing.

(56)            References Cited

OTHER PUBLICATIONS

Kumar, Narendra et al. "Molecular Dynamics Study of Thrombin Capture by Aptamers TBA26 and TBA29 Coupled to a DNA Origami," *Molecular Simulation*, vol. 44, No. 9, Mar. 14, 2018, pp. 1-8, DOI: 10.1080/08927022.2018.1448977.

Gronewold, T.M.A. et al. "Monitoring Complex Formation In The Blood-Coagulation Cascade Using Aptamer-Coated SAW Sensors," *Biosensors & Bioelectronics*, vol. 20, No. 10, Apr. 15, 2005, pp. 2044-2052, DOI: 10.1016/j.bios.2004.0.007.

Vorobyeva, Mariya et al. "Multivalent Aptamers: Versatile Tools for Diagnostic and Therapeutic Applications," *Molecules*, vol. 21, No. 12, Nov. 26, 2016, pp. 1-21, DOI: 10.3390/molecules21121613.

Lai, Pei-Xin et al. "Self-Assembled, Bivalent Aptamers on Graphene Oxide as an Efficient Anticoagulant," *Biomaterials Science*, vol. 6, No. 7, May 22, 2018, pp. 1882-1891, DOI: 10.1039/c8bm00288f.

International Search Report and Written Opinion for Patent Cooperation Treaty Application No. PCT/US2023/061059, dated Sep. 8, 2023, 16 pages.

Carlson, et al., "Behavior of Antithrombin I11 Isoforms on Immobilized Heparins", *The Journal of Biological Chemistry*, vol. 263, No. 5, pp. 2187-2194, Apr. 27, 1987.

Cañizares-Macías, et al., "Implementing Stepwise Solvent Elution in 12-15 Multisyringe Liquid Chromatography (MSC) to Separate Norepinephrine, Epinephrine and Dopamine", *Mexican Chemical Society Journal*, vol. 56, No. 2, Apr. 4, 2012, (7 pages).

Partial Supplementary European Search Report for Application No. 23743981.5, dated Dec. 10, 2025, 14 pages.

200 mM TBA15-F9

TBA15-F9+TBA29-D9 + thrombin (1:1:1) + 1.00 g/L Heparin

TBA15-F9+TBA29-D9 + thrombin (1:1:1) + 0.50 g/L Heparin

TBA15-F9+TBA29-D9 + thrombin (1:1:1)

TBA15-F9+TBA29-D9 + thrombin (1:1:1) + 0.25 g/L Heparin

TBA15-F9+TBA29-D9 + thrombin (1:1:1) + 2.00 g/L Heparin

APTAMER BASED SYSTEM TO QUANTIFY ANTI-THROMBIN III IN BLOOD

CROSS-REFERENCE TO RELATED APPLICATIONS

This application is a national phase filing of International Application No. PCT/US2020/055484, filed Oct. 14, 2020, which claims the benefit of U.S. Provisional Application No. 62/915,107, filed Oct. 15, 2019. Each of the foregoing applications is hereby incorporated herein by reference in its entirety.

SEQUENCE LISTING

The Sequence Listing written in file 694978_SeqListing_ST25.txt is 5 kilobytes in size, was created Sep. 30, 2020, and is hereby incorporated by reference

INTRODUCTION

Anti-thrombin (ATIII) is a circulating serpin (serine protease inhibitor) protein produced by the liver that functions as a modulator/buffer of inflammation and coagulation. ATIII inhibits inflammation and coagulation by binding to and inhibiting thrombin. If humans are born with <20% ATIII activity they exhibit severe hypercoagulability and most die within the first few days of birth. Levels between 30-60% are associated with chronic and sometime acute life-threatening conditions. ATIII deficiency is one of the most common causes of deep venous thrombosis and spontaneous pulmonary embolism.

Heparin is the most commonly utilized intravenous agent for anticoagulation in hospitals today. Heparin acts as an anticoagulant through its interaction with ATIII. Anti-thrombin activity of ATIII is increased 2000-4000 fold by binding the heparin. Approximately 15% of all patients entering a hospital receive heparin at some time during their visit. It is required for heart-lung machine use. In heart and vascular surgery, heparin is given in moderate to large dosages (250-600 u/Kg of heparin). Smaller dosages are utilized routinely for procedures such as cardiac catheterization, renal dialysis and many other blood filtration or radiology procedures.

Patient response to heparin is highly variable because of polymorphisms in the population and because various diseases, injuries, conditions, or medications can decrease circulating ATIII. In particular, heparin treatment results in decreased circulating ATIII. In heart surgery, the variability of human response to heparin is a major problem. In patients with low ATIII, heparin fails to function adequately as an anticoagulant. Such patients require administration of exogenous ATIII. Antithrombin supplementation results in better survival in cardiac surgery patients. However, excess anti-thrombin can lead to deleterious bleeding events. Ideally, the level of ATIII in a subject would be determined prior to administration of heparin or ATIII. Currently there are no reliable means to predict, or quickly measure ATIII levels in a subject. Existing tests for ATIII indirectly assess anti-Xa activity in the presence or absence of heparin or utilize enzyme or immuno assays that a complex and/or infrequently run in hospital setting.

SUMMARY

Described are compounds, compositions, and kits useful for determining the level of anti-thrombin III (ATIII) in a sample. The compounds, compositions, and kits comprise signaling aptamers that bind to thrombin and produce a detectable signal in the presence of ATIII. In some embodiments, the signaling aptamers comprise a first thrombin-specific aptamer containing a fluorescent label and a second thrombin-specific aptamer containing a quencher. In some embodiments, the signaling aptamers are provided bound to thrombin in a thrombin-signaling aptamer complex. When bound to thrombin, hybridizing sequences present on each of the signaling aptamers hybridize to form a duplex region. Formation of the duplex places the fluorescent label in proximity to the quencher, resulting in decreased fluorescence of the fluorescent label. In the presence to ATIII, the ATIII binds to the thrombin and displaces the first signaling aptamer, the second signaling aptamer, or both signaling aptamers. The displacing of the signaling the aptamer(s) results in an increase in fluorescence signal. The increase in fluorescence signal can be measured and used to detect and/or quantify ATIII in a sample.

Methods of using the described compounds, compositions, and kits to detect and/or quantify the amount of ATIII in a sample are also described. In some embodiments, the methods comprise: forming a thrombin-signaling aptamer complex comprising thrombin, a first signaling aptamer, and a second signaling aptamer, contacting the thrombin-signaling aptamer complex with a sample containing or suspected of containing ATIII, and measuring fluorescence emitted by the fluorescent label. In some embodiments, the methods comprise contacting a thrombin-signaling aptamer complex with a sample containing or suspected of containing ATIII and detecting or measuring an increase in fluorescence signal emitted by the fluorescent label. In some embodiments, the increase in fluorescence signal is proportional to the level of ATIII in the sample.

In some embodiments, the described compounds, compositions, kits, and methods can be used to determine the dosage of heparin and/or exogenous ATIII to administer to a subject prior to, concurrent with, or subsequent to a medical procedure.

DESCRIPTION

A. Definitions

Figure 1:
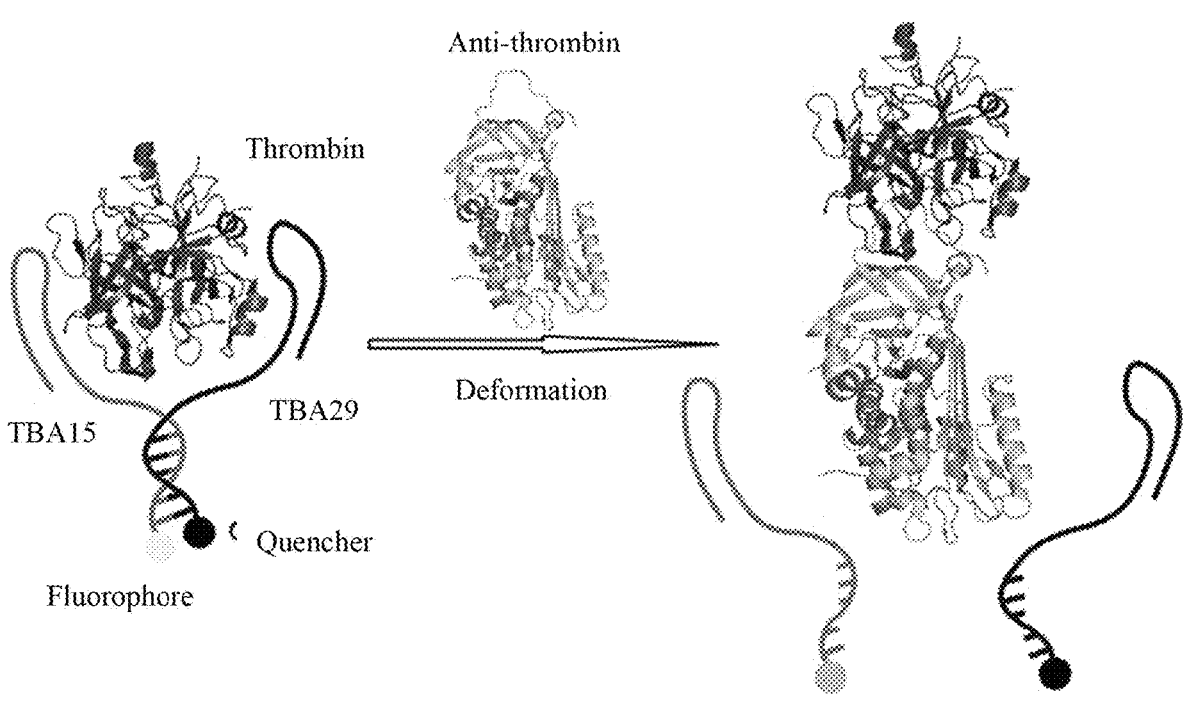
FIG. 1 is an illustration of ATIII (anti-thrombin) binding to a thrombin-signaling aptamer complex and displacing both the first (TBA15) and second (TBA29) signaling aptamers. For some signaling aptamer pairs, ATIII binding to thrombin results in dissociation of the first (e.g., TBA15) signaling aptamer.

Before describing the present teachings in detail, it is to be understood that the disclosure is not limited to specific compositions or process steps, as such may vary. It should be noted that, as used in this specification and the appended claims, the singular form "a," "an," and "the" include plural references unless the context clearly dictates otherwise. Thus, for example, reference to "an oligomer" includes a plurality of oligomers and the like. The conjunction "or" is to be interpreted in the inclusive sense, i.e., as equivalent to "and/or," unless the inclusive sense would be unreasonable in the context.

In general, the term "about" indicates insubstantial variation in a quantity of a component of a composition not having any significant effect on the activity or stability of the composition. When the specification discloses a specific value for a parameter, the specification should be understood as alternatively disclosing the parameter at "about" that value. All ranges are to be interpreted as encompassing the endpoints in the absence of express exclusions such as "not including the endpoints"; thus, for example, "within 10-15" includes the values 10 and 15. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components. Embodiments in the specification that recite "consisting essentially of" various components are also contemplated as "consisting of". "Consisting essentially of" means that additional component(s), composition(s) or method step(s) that do not materially change the basic and novel characteristics of the compositions and methods described herein may be included in those compositions or methods.

"Aptamers" are short (often less than 40 nucleobases in length) single-stranded polynucleotide molecules that selectively bind to specific molecular targets, such as proteins or protein epitopes. Aptamers are readily produced by chemical syntheses. Aptamers can possess desirable storage properties. In some embodiments, the aptamer elicits little or no immunogenicity in therapeutic applications.

A "signaling aptamer" is an aptamer linked to a hybridizing sequence and a label. The hybridizing sequence can be linked to the 5' or 3' end of the aptamer. In some embodiments, the hybridizing sequence is linked to the aptamer via a linker. In some embodiments, the label is linked to a hybridizing sequence.

A "hybridizing sequence" is a short (generally 6-12 nucleotides in length) single stranded polynucleotide capable of base pairing with a complementary hybridizing sequence. In some embodiments, a first signaling aptamer is linked to a first hybridizing sequence that is complementary a second hybridizing sequence linked to a second signaling aptamer. The first and second hybridizing sequences can base pair (hybridize) to form a duplex region.

A "label" is a detectable molecule and/or a quencher. Detectable molecules include, but are not limited to, fluorescent labels. A fluorescent label (fluorophore) is a fluorescent chemical compound that can re-emit light upon light excitation. Fluorescent labels absorb light energy of a specific wavelength and re-emit light at a longer wavelength. A quencher is a compound that decreases the fluorescence intensity of a fluorescent label. A quencher can absorb excitation energy emitted from a fluorescent molecule and dissipate the energy as heat or as a longer wavelength light. When a fluorescent label and a quencher are in sufficiently close proximity, the fluorescent label's emission is suppressed.

A fluorescent label can be, but is not limited to: xanthenes, FITC, FAM™, TET™, CAL FLUOR™ (Orange or Red), ALEXA FLUOR™, QUASAR™, fluorescein, hexochloro-fluorescein (HEX), rhodamine, Carboxy-X-Rhodamine (ROX), tetramethylrhodamine, IAEDANS, EDANS, coumarin, BODIPY FL, lucifer yellow, eosine, erythrosine, Texas Red, cyanines, or CY dyes (e.g., Cy3, Cy3.5, Cy5, Cy5.5).

A quencher can be, but is not limited to, DABCYL, BLACK HOLE QUENCHERs™ (BHQ™, e.g., Black Hole Quencher-0, Black Hole Quencher 1, Black Hole Quencher 2, Black Hole Quencher 3, Black Hole Quencher 650), or TAMRA™ compounds.

Exemplary fluorescent label/quencher pairs include, but are not limited to, fluorescein and dabcyl, fluorescein and black hole quencher, eosine and DABCYL, coumarin/DABCYL, CY5 and Black Hole Quencher 1, CY5 and Black Hole Quencher 2, CY3 and Black Hole Quencher 1, CY3 and Black Hole Quencher 2

A "linker" or linking group is a connection between two atoms that links one chemical group or segment of interest (e.g., an aptamer) to another chemical group or segment of interest (e.g., a hybridizing sequence) via one or more covalent bonds. In some embodiments, a linker increases the distance between the two atoms. In some embodiments, a linker is a flexible linker that adds flexibility to the linkage. Linkers include, but at not limited to, alkyl groups, alkenyl groups, alkynyl groups, aryl groups, aralkyl groups, aralkenyl groups, and aralkynyl groups (each of which can contain one or more heteroatoms), heterocycles, amino acids, nucleotides, saccharides, and polymeric groups. Polymeric groups include, but are not limited to, polyethylene glycol. In some embodiments, a linker comprises $PEG_n$, wherein n is an integer from 1 to 50. In some embodiments, the linker comprises $PEG_1$, $PEG_2$, $PEG_3$, $PEG_4$, $PEG_5$, $PEG_6$, $PEG_7$, $PEG_8$, $PEG_9$, or $PEG_{10}$. The linker does not interfere with binding of the aptamer to its molecular target (e.g., thrombin). The linker can facilitate duplex formation by complementary hybridizing sequences when two aptamers containing complementary hybridization sequences are bound to a target molecule.

The "sample" includes any physiological fluid derived from a subject. Samples include, but are not limited to, blood, serum, plasma, and fractions thereof. A sample can be pretreated prior to use, such as preparing plasma from blood. A sample may be used directly as obtained from the subject or following a pretreatment to modify the character of the sample. Pretreatments include, but are not limited to, filtration, dilution, and addition of one or more reagents useful in preparing or analyzing the sample. Sample includes the original sample or an original sample that has received one or more pretreatments. A sample may be of any suitable size or volume. In some embodiments, the sample volume is less than or equal to 1 mL, less than or equal to 500 μL, less than or equal to 250 μL, less than or equal to 100 μL, less than or equal to 75 μL, less than or equal to 50 μL, less than or equal to 35 μL, less than or equal to 25 μL, or less than or equal to 20 μL.

"Thrombin" is a serine protease. In humans, thrombin is encoded by the F2 gene. Prothrombin (coagulation factor II) is proteolytically cleaved to form thrombin in the clotting process. Thrombin in turn acts as a serine protease that converts soluble fibrinogen into insoluble strands of fibrin, as well as catalyzing other coagulation-related reactions. Thrombin is inactivated by antithrombin III.

B. Signaling Aptamers

Described are compounds, compositions, kits, and methods for detecting and/or quantifying the level of ATIII in a sample.

In some embodiments, the compounds and compositions comprise one or more signaling aptamers that bind to thrombin and produce a detectable signal in the presence of ATIII. In some embodiments, the compounds, compositions, and kits comprise a first signaling aptamer and a second signaling aptamer that each bind to thrombin. The first and second signaling aptamers bind to different epitopes on thrombin. In some embodiments, the first aptamer contains a detectable label, such as a fluorescent label, and the second aptamer contains a quencher that reduces or alters fluorescence of the fluorescent label. In some embodiments, the second aptamer contains a detectable label, such as a fluorescent label, and the first aptamer contains a quencher that reduces or alters fluorescence of the fluorescent label. The first and second signaling aptamers are configured such that the quencher quenches signal from the fluorescent label when both signaling aptamers are bound to thrombin. The first and second signaling aptamers are further designed such that ATIII binding to thrombin results in dissociation of at least one of the aptamers from the thrombin. Dissociation of the signaling aptamer from thrombin results in dequenching of the fluorescent label and an increase in detectable signal (i.e., fluorescence).

The first and second signaling aptamers contain hybridization sequences that are able to from a duplex region when the signaling aptamers are bound to thrombin. In some embodiments, the labels on the signaling aptamers are linked to the hybridization sequences. In some embodiments, the hybridization sequences are designed to position the fluorescent label in close proximity with the quencher when the hybridization sequences base pair to form a duplex. The hybridization sequences form a sufficiently stable duplex such that the fluorescent label is quenched when the signaling aptamers are bound to thrombin in the absence of ATIII. In some embodiments, the hybridization sequences are further designed such that binding of ATIII to thrombin results in dequenching and an increase in fluorescence.

In some embodiments, the signaling aptamers contain a linker between the aptamer sequence and the hybridization sequence. The linker can be used to increase spacing between the aptamer sequence and the hybridization sequence and/or to add flexibility between the aptamer sequence and the hybridization sequence. The linker is designed to facilitate duplex formation between hybridization sequences when the signaling aptamers are bound to thrombin.

In some embodiments, a first signaling aptamer contains the aptamer nucleotide sequence of thrombin aptamer TBA15. TBA15 is a 15-mer single stranded DNA having the sequence 5'-GGTTGGTGTGGTTGG-3' (SEQ ID NO: 1). The TBA15 aptamer binds the exosite I epitope of thrombin with a Kd of about 100 nM. Exosite I is the binding site of fibrinogen on thrombin. In other embodiments, the first signaling aptamer contains the aptamer nucleotide sequence of thrombin aptamer TBA29 (described in more detail below). In some embodiments, the first signaling aptamer comprises a first hybridizing sequence linked to the 3' end of the aptamer. In some embodiments, the first hybridizing sequence is linked to the 3' end of the aptamer via a linker. In some embodiments, the linker comprises a PEG. In some embodiments, the PEG comprises PEG$_{1-10}$ (e.g., —(CH$_2$—CH$_2$—O)$_{1-10}$—). In some embodiments, the PEG comprises PEG$_6$. In some embodiments, the first signaling aptamer comprises a fluorescent molecule linked to the first hybridizing sequence. In some embodiments, the first signaling aptamer comprises a fluorescent molecule linked to the 3' end of the first hybridizing sequence.

In some embodiments, a second signaling aptamer contains the aptamer nucleotide sequence of thrombin aptamer TBA29. TBA29 is a 29-mer single stranded DNA having the sequence 5'-AGTCCGTGGTAGGGCAGGTTGGGGTGACT-3' (SEQ ID NO: 2). The TBA29 aptamer binds the exosite II epitope of thrombin with a Kd of about 0.5 nM. The exosite II epitope is involved in the activation of factor V/VIII and mediates the heparin binding. In other embodiments, the second signaling aptamer contains the aptamer nucleotide sequence of thrombin aptamer TBA15. In some embodiments, the second signaling aptamer comprises a second hybridizing sequence linked to the 5' end of the aptamer. In some embodiments, the second hybridizing sequence is linked to the 5' end of the aptamer via a linker. In some embodiments, the linker comprises a PEG. In some embodiments, the PEG comprises PEG$_{1-10}$ (e.g., —(CH$_2$—CH$_2$—O)$_{1-10}$—. In some embodiments, the PEG comprises PEG$_6$. In some embodiments, the second signaling aptamer comprises a quencher linked to the second hybridizing sequence. In some embodiments, the second signaling aptamer comprises a quencher linked to the 5' end of the second hybridizing sequence.

Other thrombin-binding aptamers can be identified using methods known in the art. Such methods include, but are not limited to, systematic evolution of ligands by exponential enrichment (SELEX) and automated in vitro selection.

In some embodiments, the hybridizing sequences of the signaling aptamers are 5-20 nucleobases in length. In some embodiments, the hybridizing sequences of the signaling aptamers are 5, 6, 7, 8, 9, 10, 11, 12, 13, 14, 15, 16, 17, 18, 19, or 20 nucleobases in length. In some embodiments, the hybridizing sequences of the signaling aptamers are 6-10 nucleobases in length. In some embodiments, the hybridizing sequences of the signaling aptamers are 6, 7, 8, 9, or 10 nucleobases in length. In some embodiments, the hybridizing sequences of the signaling aptamers are 9 nucleobases in length.

In some embodiments, the hybridizing sequences of the signaling aptamers hybridize to form a duplex 6-10 base pairs in length. In some embodiments, the hybridizing sequences of the signaling aptamers hybridize to form a duplex 6, 7, 8, 9, or 10 base pairs in length. In some embodiments, the hybridizing sequence of the signaling aptamers hybridize to form a duplex 9 base pairs in length.

In some embodiments, a first signaling aptamer comprises a first hybridizing sequence of wherein each N is independently any nucleobase and n is an integer from 6-10, and a second signaling aptamer comprises a second hybridizing sequence that is complementary to the first hybridizing sequence. In some embodiments, the hybridized duplex contains four G:C base pairs and 5 A:T base pairs.

In some embodiments, the hybridizing sequences of the signaling aptamers comprise or consist of the sequence 5'-GTCGTA-3' (SEQ ID NO: 3) or 5'-TACGAC-3' (SEQ ID NO: 4). In some embodiments, the first and second hybridizing sequences of the signaling aptamers comprise or consist of the sequences 5'-GTCGTA-3' (SEQ ID NO: 3) and 5'-TACGAC-3' (SEQ ID NO: 4).

In some embodiments, the hybridizing sequences of the signaling aptamers comprise or consist of the sequence 5'-GTCGTAT-3' (SEQ ID NO: 5) or 5'-ATACGAC-3' (SEQ ID NO: 6). In some embodiments, the first and second hybridizing sequences of the signaling aptamers comprise or consist of the sequences 5'-GTCGTAT-3' (SEQ ID NO: 5) and 5'-ATACGAC-3' (SEQ ID NO: 6).

In some embodiments, the hybridizing sequences of the signaling aptamers comprise or consist of the sequence 5'-GTCGTAGT-3' (SEQ ID NO: 7) or 5'-ACTACGAC-3' (SEQ ID NO: 8). In some embodiments, the first and second hybridizing sequences of the signaling aptamers comprise or consist of the sequences 5'-GTCGTAGT-3' (SEQ ID NO: 7) and 5'-ACTACGAC-3' (SEQ ID NO: 8).

In some embodiments, the hybridizing sequences of the signaling aptamers comprise or consist of the sequence 5'-GTCGTAAGT-3' (SEQ ID NO: 9) or 5'-ACTTACGAC-3' (SEQ ID NO: 10). In some embodiments, the first and second hybridizing sequences of the signaling aptamers comprise or consist of the sequences 5'-GTCGTAAGT-3' (SEQ ID NO: 9) and 5'-ACTTACGAC-3' (SEQ ID NO: 10).

In some embodiments, the hybridizing sequences of the signaling aptamers comprise or consist of the sequence 5'-GTCGTAAGCT-3' (SEQ ID NO: 11) or 5'-AGCT-TACGAC-3' (SEQ ID NO: 12). In some embodiments, the first and second hybridizing sequences of the signaling aptamers comprise or consist of the sequences 5'-GTCGTAAGCT-3' (SEQ ID NO: 11) and 5'-AGCT-TACGAC-3' (SEQ ID NO: 12).

In some embodiments, the hybridizing sequences of the signaling aptamers consist of the sequence 5'-GTCGTAAGT-3' (SEQ ID NO: 9) or 5'-ACTTACGAC-3' (SEQ ID NO: 10). In some embodiments, the TBA15 signaling aptamer contains a 3' hybridizing sequence consisting of 5'-GTCGTAAGT-3' (SEQ ID NO: 9). In some embodiments, the TBA15 signaling aptamer contains a 3' hybridizing sequence consisting of 5'-ACTTACGAC-3' (SEQ ID NO: 10). In some embodiments, the TBA29 signaling aptamer contains a 5' hybridizing sequence consisting of 5'-GTCGTAAGT-3' (SEQ ID NO: 9). In some embodiments, the TBA29 signaling aptamer contains a 5' hybridizing sequence consisting of 5'-ACTTACGAC-3' (SEQ ID NO: 10). In some embodiments, the TBA15 signaling aptamer contains a 3' hybridizing sequence consisting of 5'-GTCGTAAGT-3' (SEQ ID NO: 9) and the TBA29 signaling aptamer contains a 5' hybridizing sequence consisting of 5'-ACTTACGAC-3' (SEQ ID NO: 10). In some embodiments, the TBA15 signaling aptamer contains a 3' hybridizing sequence consisting of 5'-ACT-TACGAC-3' (SEQ ID NO: 10) and the TB A29 signaling aptamer contains a 5' hybridizing sequence consisting of 5'-GTCGTAAGT-3' (SEQ ID NO: 9).

In some embodiments, a signaling aptamer contains a linker between the protein binding region (aptamer) and the hybridizing sequence. In some embodiments, the linker is a flexible linker. The linker can be a nucleobase linker or a non-nucleobase linker. A non-nucleobase linker can be, but is not limited to, a PEG or an aliphatic chain. In some embodiments, the linker is a PEG group. The PEG group can be (PEG)$_n$, wherein n is an integer from 1 to 20. In some embodiments, n is 1, 2, 3, 4, 5, 6, 7, 8, 9, 10, 11, 12, 13, 14, 15, 16, 17, 18, 19, or 20. In some embodiments, n is 6.

In some embodiments, a first signaling aptamer containing a first hybridizing sequence and a fluorescent label is paired with a second signaling aptamer containing a second hybridizing sequence complementary to the first hybridizing sequence and a quencher that reduces or alters fluorescence emitted by the fluorescent label.

C. Compositions

In some embodiments, thrombin-signaling aptamer complexes are described. Thrombin-signaling aptamer complexes comprise thrombin bound by the described first and second signaling aptamers. In some embodiments, the thrombin-signaling aptamer complexes are in a composition. The composition can contain one or more components that facilitate detection or measurement of fluorescence.

Thrombin can be prepared by a variety of methods known in the art, and the term "thrombin" is not intended to imply a particular method of production. The thrombin can be purified from a naturally occurring source, recombinant, synthetic, or synthesized from cells, such as bacteria, insect, yeast or mammalian cells, in culture. Thrombin can be purified from plasma. Both human and non-human thrombins can be used within the present invention. In some embodiments, the thrombin is human thrombin.

The thrombin-signaling aptamer complex can be provided in a solution or a lyophilized powder or cake. The thrombin-signaling aptamer complex can also be provided on a solid support, such as a test strip. In some embodiments, the signaling aptamers can be provided in a solution at a concentration of about 100 nM to about 400 nM. In some embodiments, the signaling aptamers can be provided in a solution at a concentration of about 100 nm, about 200 nM, about 300 nm, or about 400 nM. In some embodiments, the signaling aptamers can be provided in a solution at a concentration of about 200 nM. In some embodiments, the thrombin-signaling aptamer complex can be provided in a solution at a concentration of about 100 nM to about 400 nM. In some embodiments, the thrombin-signaling aptamer complex can be provided in a solution at a concentration of about 100 nm, about 200 nM, about 300 nm, or about 400 nM. In some embodiments, the thrombin-signaling aptamer complex can be provided in a solution at a concentration of about 200 nM.

In some embodiments, the molar ratio of the first signaling aptamer to the second signaling aptamer is about 1:1. In some embodiments, the molar ratio of first and second signaling aptamers to thrombin is about 1:1:2 to 2:2:1 (first signaling aptamer:second signaling aptamer:thrombin). In some embodiments, the molar ratio of first and second signaling aptamers to thrombin is about 1:1:1 (first signaling aptamer:second signaling aptamer:thrombin). In some embodiments, the molar ratio of TBA15 signaling aptamer to TBA29 signaling aptamer is about 1:1. In some embodiments, the molar ratio of the TBA15 signaling aptamer and TBA29 signaling aptamer to thrombin is about 1:1:2 to 2:2:1 (TBA15 signaling aptamer:TBA29 signaling aptamer:thrombin). In some embodiments, the molar ratio of TBA15 signaling aptamer and TBA29 signaling aptamer to thrombin is about 1:1:1 (TBA15 signaling aptamer:TBA29 signaling aptamer:thrombin).

When a sample containing ATIII is added to a thrombin-signaling aptamer complex or a composition containing the thrombin-signaling aptamer complex, the ATIII binds to the thrombin, leading to dissociation of thrombin-signaling aptamer complex and an increase in fluorescence from the fluorescent label present on one of the signaling aptamers. The increase in fluorescence is proportional to the amount of ATIII in the sample. Dissociation of thrombin-signaling aptamer complex includes dissociation of the first signaling aptamer, the second signaling aptamer, or both signaling aptamers from the thrombin. In some embodiments, ATIII binding to thrombin dissociates the first signaling aptamer.

In some embodiments, the level of ATIII in the sample is determining by comparing the increase in fluorescence with a standard curve. The standard curve can be obtained by determining the level of increase in fluorescence for various known concentration of ATIII when measured under the same conditions.

D. Kits

Also provided are kits comprising one or more reagents utilized in performing a method disclosed herein or kits comprising one or more compounds or compositions disclosed herein. Such kits may be diagnostic in nature.

Kits will generally comprise a described pair of signaling aptamers or thrombin-signaling aptamer complexes in a suitable container or receptacle. The kits may also contain additional reagents or devises useful in determining the level of ATIII in a sample. Such additional reagents or devices can be, but are not limited to, one or more of: buffer, ATIII, syringe, and hypodermic needle. The kits can be used to quantify the level of ATIII in one or more samples. The containers can be formed from a variety of materials including, but not limited to, glass and pharmaceutically compatible plastics.

In some embodiments, a kit comprises one or more containers comprising one or more of any of the described signaling aptamers or complexes. In some embodiments, a kit contains or more more test strips comprising one or more of any of the described signaling aptamers or complexes. In some embodiments, a kit contains a unit dosage, meaning a predetermined amount of a composition comprising, for example, any of the described signaling aptamers or complexes suitable for determining the level of ATIII in a sample, optionally, with one or more additional reagents. In some embodiments, the kit contains one or more control samples.

In some embodiments, the signaling aptamers or thrombin-signaling aptamer complexes are provided in a liquid. The liquid can be sterile or not sterile. In some embodiments, the signaling aptamers or thrombin-signaling aptamer complexes are provided in a lyophilized form that can be reconstituted upon addition of an appropriate solvent. The solvent used for reconstitution can be provided in a separate container.

In some embodiments, a kit comprises a label, marker, package insert, bar code and/or reader indicating that the kit contents may be used determine the level of ATII in a sample. In some embodiments, a kit can contain instructional material which describes use of the kit to measure the level of ATIII in a sample.

E. Methods

Described are methods of using the described compounds and compositions to detect and/or quantify the amount of ATIII in a sample. In some embodiments, the methods comprise: forming a thrombin-signaling aptamer complex comprising thrombin, a first signaling aptamer, and a second signaling aptamer, contacting the thrombin-signaling aptamer complex with a sample containing or suspected of containing ATIII, and measuring fluorescence emitted by the fluorescent label. In some embodiments, the methods comprise contacting a thrombin-signaling aptamer complex with a sample containing or suspected of containing ATIII and detecting or measuring an increase in fluorescence signal emitted by the fluorescent label. In some embodiments, the increase in fluorescence signal is proportional to the level of ATIII in the sample.

The described methods for determining the level of ATIII in a sample are rapid, simple, and accurate. The methods can be performed prior to, concurrent with, and/or subsequent to a medical procedure. Medical procedures include, but are not limited to, cardiac surgery, vascular surgery, heart-lung machine bypass, cardiac catheterizations, dialysis, extracorporeal membrane oxygenation, filtration procedures, and radiology procedures.

In some embodiments, described compounds, compositions, and methods can be used to determine the level of ATIII in a subject within about 10%, within about 9%, within about 8%, within about 7%, within about 6%, within about 5%, within about 4%, within about 3%, within about 2%, or within about 1%. In some embodiments, described compounds, compositions, and methods can be used to determine the level of ATIII in a subject within about 5%. In some embodiments, the methods can be used to measure the level of ATIII in a sample in less than or equal to 30 min, less than or equal to 25 min, less than or equal to 20 min, less than or equal to 15 min, or less than or equal to 10 min.

In some embodiments, the described methods are used to determine if a subject is ATIII deficient. In some embodiments, the described methods are used to determine a dosage of heparin and/or exogenous ATIII to administer to a patient.

In some embodiments, the level of ATIII measure in sample is compared with a predetermined control or level. The predetermined control or level can be derived from a population of subjects known to respond to heparin and/or known to be deficient in ATIII. In some embodiments, a value less than the predetermined control indicates the subject is deficient in ATIII and would benefit from administration of exogenous ATIII. In some embodiments, if the level ATII in the sample is lower than a predetermined level, then exogenous ATIII is administered to the subject. In some embodiments, a value higher than the predetermined control indicates the subject is not deficient in ATIII and is likely to respond to heparin treatment. In some embodiments, if the level ATII in the sample is higher than a predetermined level, then heparin is administered to the subject.

Described are methods of treating a patient with an anticoagulant comprising: obtaining a serum, plasma, or blood sample from the patient; contacting the sample with a described thrombin-signaling aptamer complex; measuring an increase in fluorescence; and determining a level of ATIII in the sample based on the increase in fluorescence; and administering to the patient heparin and/or exogenous ATIII based on the determined level of ATIII in the sample.

F. Listing of Embodiments

1. A kit for determining the level of anti-thrombin (ATIII) in a subject, comprising:
   (a) a first signaling aptamer comprising a first thrombin-specific aptamer, a first hybridization sequence, and a fluorescent label; and
   (b) a second signaling aptamer comprising a second thrombin-specific aptamer, a second hybridization sequence, and a quencher,
   wherein the first and second hybridization sequences are complementary to each other, and wherein fluorescence of the fluorescent label is quenched when the first and second thrombin-specific signaling aptamers are bound to thrombin.

2. The kit of embodiment 1, wherein the first thrombin-specific aptamer comprises TBA15.

3. The kit of embodiment 1 or 2, wherein the second thrombin-specific aptamer comprises TBA29.

4. The kit of any one of embodiments 1-3, wherein the first and second hybridization sequences are 6-10 nucleobases in length.

5. The kit of embodiment 4, wherein the first and second hybridization sequences are 9 nucleobases in length.

6. The kit of any one of embodiments 1-5, wherein the first hybridization sequence comprises the sequence 5'-GTCGTA-3' and the second hybridization sequence comprises 5'-TACGAC-3' or the first hybridization sequence comprise the sequence 5'-TACGAC-3' and the second hybridization sequence comprises 5'-GTCGTA-3'.

7. The kit of embodiment 6, wherein the first hybridization sequence comprises the sequence 5'-GTCGTAAG-T-3' and the second hybridization sequences comprises the sequence 5'-ACTTACGAC-3' or the first hybridization sequence comprises the sequence 5'-ACTTACGAC-3' and the second hybridization sequences comprises the sequence 5'-GTCGTAAGT-3'.

8. The kit of any one of embodiments 1-7, wherein the first and/or second signaling aptamers comprises a linker, wherein the linker connects the thrombin-specific aptamer to the hybridization sequence.

9. The kit of embodiment 8, wherein the linker comprises polyethylene glycol (PEG).

10. The kit of embodiment 9, wherein the PEG is $PEG_6$.

11. The kit of any one of embodiments 1-10, wherein the fluorescent label comprises FITC, fluorescein, hexochloro-fluorescein, rhodamine, Carboxy-X-Rhodamine, tetramethylrhodamine, IAEDANS, EDANS, coumarin, BODIPY FL, lucifer yellow, eosine, erythrosine, Texas Red, or cyanine.

12. The kit of any one of embodiments 1-11, wherein the quencher comprises a DABCYL, a BLACK HOLE QUENCHER, or a TAMRA compound.

13. The kit of any one of embodiments 1-12, further comprising thrombin.

14. The kit of embodiment 13, wherein the thrombin, first signaling aptamer, and second signaling aptamer form a complex.

15. A complex comprising: a thrombin; a first signaling aptamer comprising a first thrombin-specific aptamer, a first hybridization sequence, and a fluorescent label; and a second signaling aptamer comprising a second thrombin-specific aptamer, a second hybridization sequence, and a quencher, wherein the first and second hybridization sequences are complementary to each other and form a duplex, and wherein fluorescence of the fluorescent label is quenched.

16. The complex of embodiment 15, further comprising a thrombin.

17. A method of determining the level of ATIII in a sample from a subject, comprising:
   (a) obtaining the sample from the subject;
   (b) contacting a composition containing the complex of embodiment 15 with the sample; and
   (c) measuring an increase in fluorescence of the composition,
   wherein the increase in fluorescence is proportional to the level of ATIII in the sample.

18. The method of embodiment 17, wherein the sample comprises a serum sample, blood sample, or plasma sample.

19. The method of embodiment 17 or 18, wherein the increase in fluorescence is measured in less than 15 minutes.

20. A method of treating a patient with an anticoagulant comprising:

(a) determining the level of ATIII in the patient, wherein the determining comprises the steps of:

(i) obtaining a serum, plasma, or blood sample from the patient;

(ii) contacting a composition containing the complex of embodiment 15 or 16 with the sample; and (iii) measuring an increase in fluorescence of the composition, wherein the increase in fluorescence is proportional to the level of ATIII in the sample; and (b) administering to the patient heparin and/or exogenous ATIII based on the level of ATIII in the sample determined in step (iii).

EXAMPLES

Example 1. Exemplary Signaling Aptamers

```
TBA15-F6
                                   (SEQ ID NO: 13)
(5'-GGTTGGTGTGGTTGG-(PEG)6-GTCGTA-FITC-3')

TBA29-D6
                                   (SEQ ID NO: 14)
(5'-DABCYL-TACGAC-(PEG)6-AGTCCGTGGTAGGGCAGGTTGGG

GTGACT-3'),

TBA15-F7
                                   (SEQ ID NO: 15)
(5'-GGTTGGTGTGGTTGG-(PEG)6-GTCGTAT-FITC-3')

TBA29-D7
                                   (SEQ ID NO: 16)
(5'-Dabcyl-ATACGAC-(PEG)6-AGTCCGTGGTAGGGCAGGTTGG

GGTGACT)

TBA15-F8
                                   (SEQ ID NO: 17)
(5'-GGTTGGTGTGGTTGG-(PEG)6-GTCGTAGT-FITC-3')

TBA29-D8
                                   (SEQ ID NO: 18)
(5'-Dabeyl-ACTACGAC-(PEG)6-AGTCCGTGGTAGGGCAGGTTG

GGGTGACT)

TBA15-F9
                                   (SEQ ID NO: 19)
(5'-GGTTGGTGTGGTTGG-(PEG)6-GTCGTAAGT-FITC-3')

TBA29-D9
                                   (SEQ ID NO: 20)
(5'-Dabcyl-ACTTACGAC-(PEG)6-AGTCCGTGGTAGGGCAGGTTG

GGGTGACT-3')

TBA15-F10
                                   (SEQ ID NO: 21)
(5'-GGTTGGTGTGGTTGG-(PEG)6-GTCGTAAGCT-FITC-3')

TBA29-D10
                                   (SEQ ID NO: 22)
(5'-Dabcyl-AGCTTACGAC-(PEG)6-AGTCCGTGGTAGGGCAGGTT

GGGGTGACT)
```

Example 2. Reagents

All the DNAs (Integrated DNA technologies) were stored at $-20°$ C. with Tris-HCl buffer (Tris-acetate 20 mM, KCl 5 mM, NaCl 140 mM, MgCl$_2$ 1 mM, CaCl$_2$ 1 mM, pH=7.5).

Human $\alpha$-thrombin (Haematologic Technologies, Inc.) was dissolved in the 50% glycerol/water (v/v) and stored at $-20°$ C.

Antithrombin (Grifols Therapeutics Inc.) was purchased as a powder and mixed with 10 mL deionized water, and divided into 10 vials, which were all stored at $4°$ C. The concentration was >50 times normal human antithrombin concentration.

Heparin sodium salt (Santa Cruz biotechnology) was stored at $4°$ C.

Albumin from human serum (Sigma), was stored at $4°$ C.

Example 3. Formation of Thrombin-Signaling Aptamer Complex

Thrombin was prepared at a concentration of 200 nM. The ratio between the TBA15 signaling aptamer and the TBA29 signaling aptamer was 1:1. The signaling aptamers were prepared at concentration of 100 nM, 200 nM, 300 nM and 400 nM. Thrombin-signaling aptamer complexes were formed by combining the thrombin with different concentrations of signaling aptamers. For each, the thrombin and signaling aptamer solutions were incubated together in the Tris-HCl buffer with a total volume of 100 μL at room temperature for 30 min. For controls, TBA15 signaling aptamer alone (control 1) or TBA15 signaling aptamer+ TBA29 signaling aptamer (control 2) were used. Fluorescence spectroscopy was used for detection.

Figure 3:
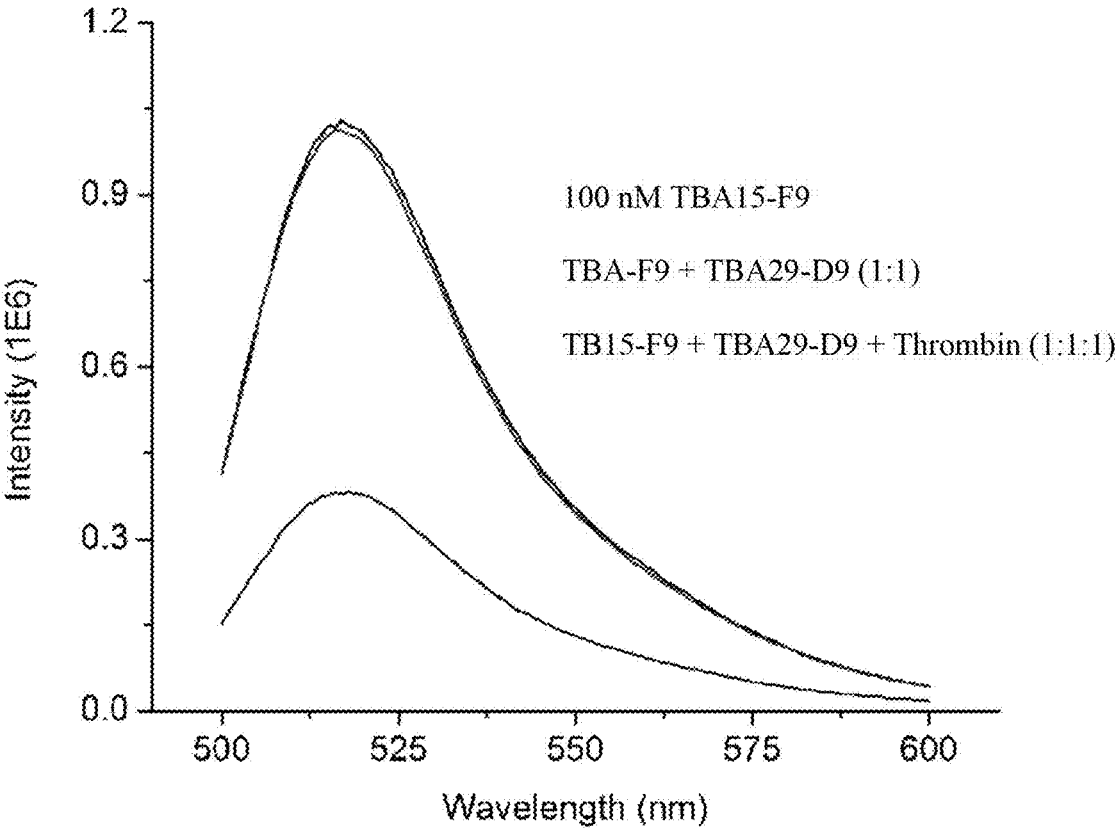
FIG. 3. Graph illustrating fluorescence intensity at varying wavelengths for 100 nM signaling aptamer concentration. Complexes in the figure legend are in order of maximum intensity (highest to lowest maximum intensity).

As shown in FIG. 3, at 100 nM concentration, peak fluorescence intensity was $3.80 \times 10^5$ for the thrombin-signaling aptamer complex and set as set as $I_{FDTHR}$. Peak fluorescence intensity for TBA15 signaling aptamer alone was $1.029 \times 10^6$ and set as $I_0$. Peak fluorescence intensity for the TBA15-F9+TAB29-D9 signaling aptamers was $1.011 \times 10^6$ and set as $I_{FD}$. The fluorescence intensity of the TBA15 signaling aptamer alone was normalized as 100%. $I_{FD}/I_0$ was 98.25%. The relative fluorescence intensity of the thrombin-signaling aptamer complex ($I_{FDTHR}/I_0$) was 36.92%.

Figure 4:
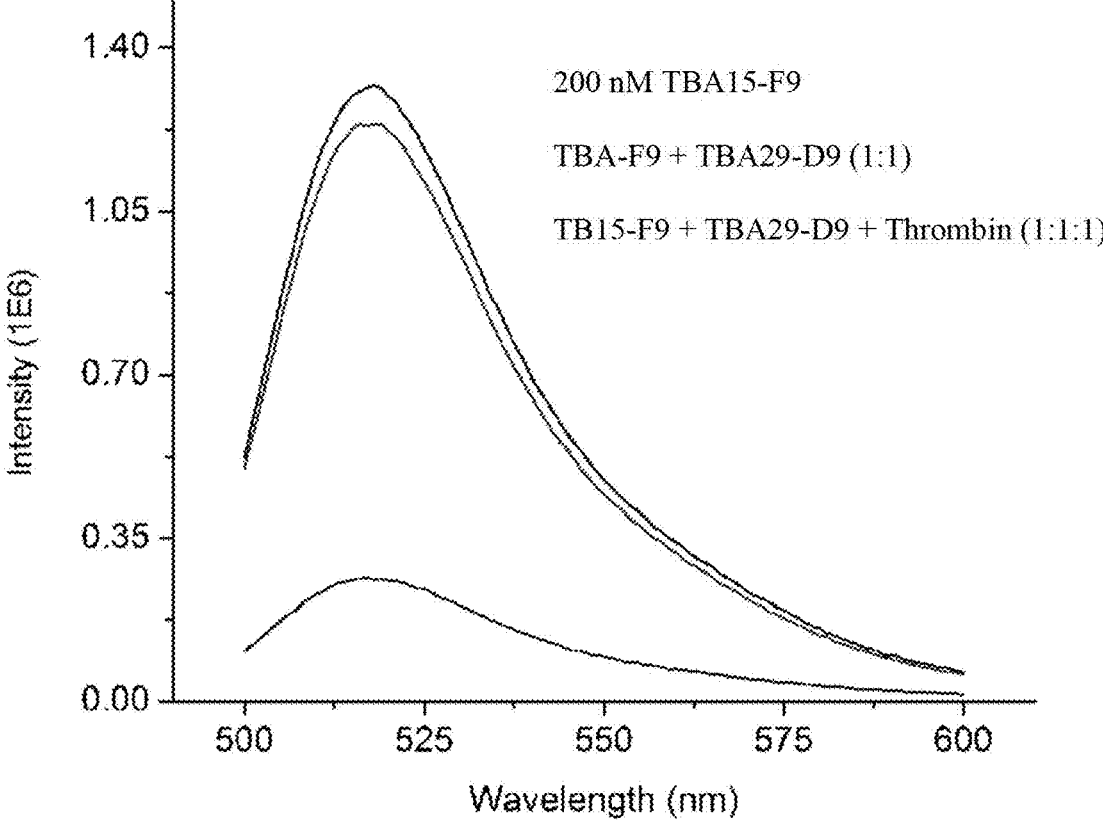
FIG. 4. Graph illustrating fluorescence intensity at varying wavelengths for 200 nM signaling aptamer concentration. Complexes in the figure legend are in order of maximum intensity (highest to lowest maximum intensity).

As shown in FIG. 4, at 200 nM concentration, peak fluorescence intensity for TBA15-F9 alone was $1.31 \times 10^6$. Peak fluorescence intensity for TBA15-F9+TBA29-D9 was $1.23H10^6$ was $2.66 \times 10^5$. Fluorescence intensity for TBA15-F9 alone was normalized as 100% and set as $I_0$. Fluorescence intensity for TBA15-F9+TBA29-D9 was set as $I_{FD}$. Then the $I_{FD}/I_0$ was 93.89%. The relative fluorescence intensity of the thrombin-signaling aptamer complex ($I_{FDTHR}/I_0$) was 20.23%.

Figure 5:
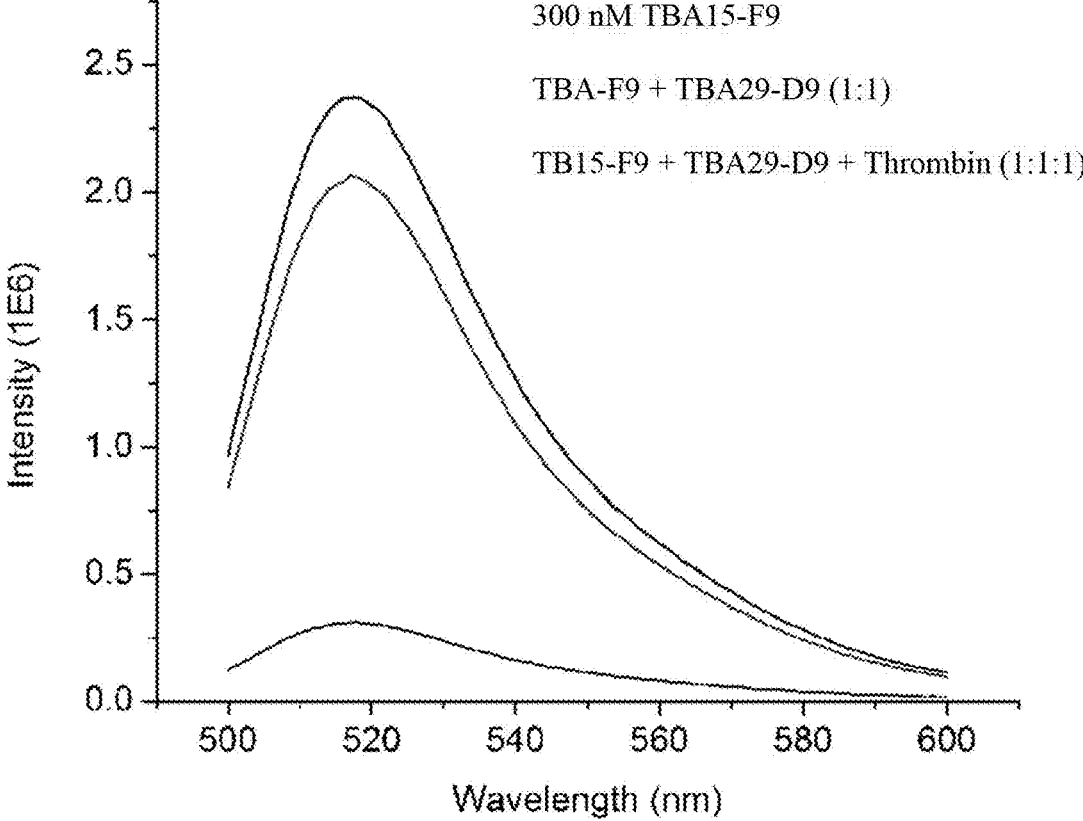
FIG. 5. Graph illustrating fluorescence intensity at varying wavelengths for 300 nM signaling aptamer concentration. Complexes in the figure legend are in order of maximum intensity (highest to lowest maximum intensity).

As shown in FIG. 5, at 300 nM concentration, peak fluorescence intensity for TBA15-F9 alone was $2.36 \times 10^6$. Peak fluorescence intensity for TBA15-F9+TBA29-D9 was $2.06 \times 10^6$. Peak fluorescence intensity for thrombin-signaling aptamer complex was $3.11 \times 10^5$. Fluorescence intensity of TBA15-F9 alone was normalized as 100% and set as $I_0$. Fluorescence intensity for TBA15-F9+TBA29-D9 was set as $I_{FD}$. Relative fluorescence intensity for TBA15-F9+ TBA29-D ($I_{FD}/I_0$) was 87.29%. The relative fluorescence intensity of the thrombin-signaling aptamer complex ($I_{FDTHR}/I_0$) was 13.17%.

Figure 6:
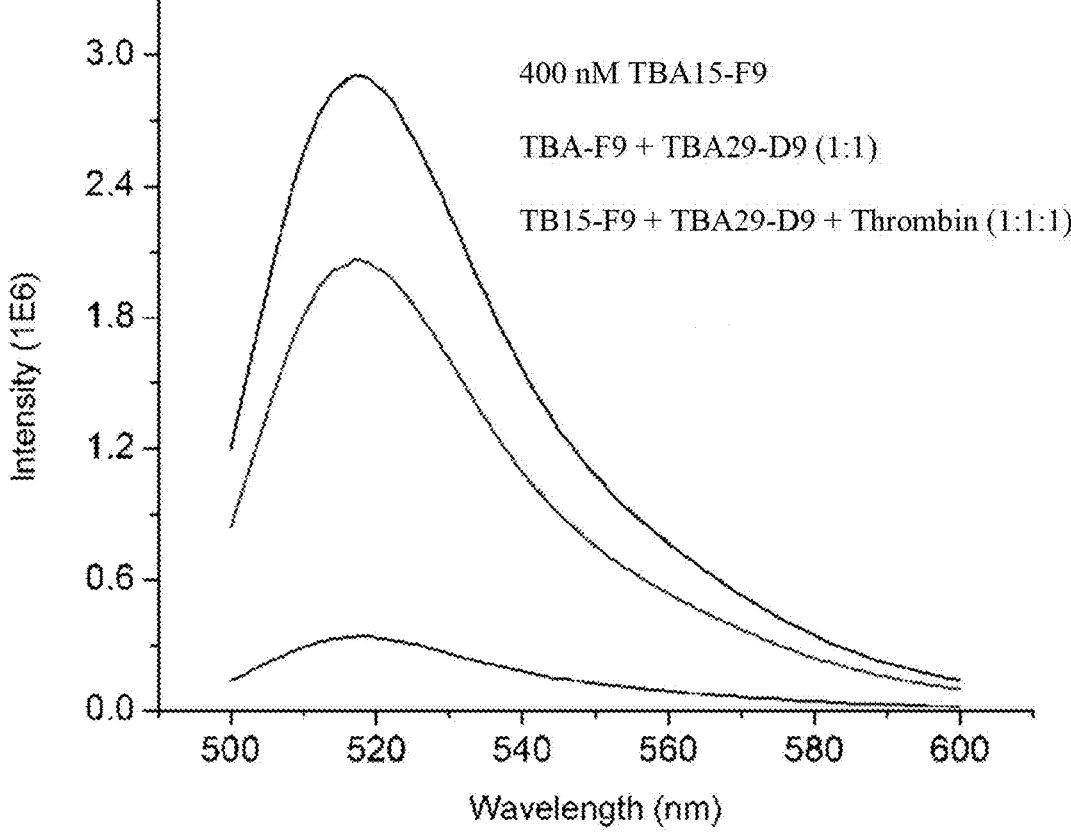
FIG. 6. Graph illustrating fluorescence intensity at varying wavelengths for 400 nM signaling aptamer concentration. Complexes in the figure legend are in order of maximum intensity (highest to lowest maximum intensity).

As shown in FIG. 6, at 400 nM concentration, peak fluorescence intensity for TBA15-F9 alone was $2.90 \times 10^6$. Peak fluorescence intensity for TBA15-F9+TBA29-D9 was $2.06 \times 10^6$. Peak fluorescence intensity for thrombin-signaling aptamer complex was $3.36 \times 10^5$. Fluorescence intensity of TBA15-F9 alone was normalized as 100% and set as $I_0$. Fluorescence intensity for TBA15-F9+TBA29-D9 was set as $I_{FD}$. Relative fluorescence intensity for TBA15-F9+

TBA29-D ($I_{FD}/I_0$) was 71.03%. The relative fluorescence intensity of the thrombin-signaling aptamer complex ($I_{FDTHR}/I_0$) was 11.58%.

Based on these experiments, a 1:1:1 ratio of thrombin to TBA15 signaling aptamer to TBA29 signaling aptamer was selected for additional experimentation (FIGS. 3-6).

Example 4. Hybridization Sequences

Five hybridization sequences (with complementary hybridization sequences) were tested for use with the signaling aptamers. The hybridization sequences were those as described for TBA15-F6+TBA29-D6, TBA15-F7+TBA29-D7, TBA15-F8+TBA29-D8, TBA15-F9+TBA29-D9, and TBA15-F10+TBA29-D10. Controls were as described above.

The TBA15 signaling aptamers and the TBA29 signaling aptamers were prepared at concentration of 200 nM and combined at a ratio of 1:1. Thrombin-signaling aptamer complexes were formed by combining the signaling aptamers with varying concentrations of thrombin. The ratio of aptamers to thrombin was (1:1:0.1 to 1:1:1.5). For each, the thrombin and signaling aptamer solutions were incubated together in the Tris-HCl buffer with a total volume of 100 μL at room temperature for 30 min. For controls, TBA15 signaling aptamer alone or TBA15 signaling aptamer+ TBA29 signaling aptamer were used. Fluorescence spectroscopy was used for detection.

Figure 7:
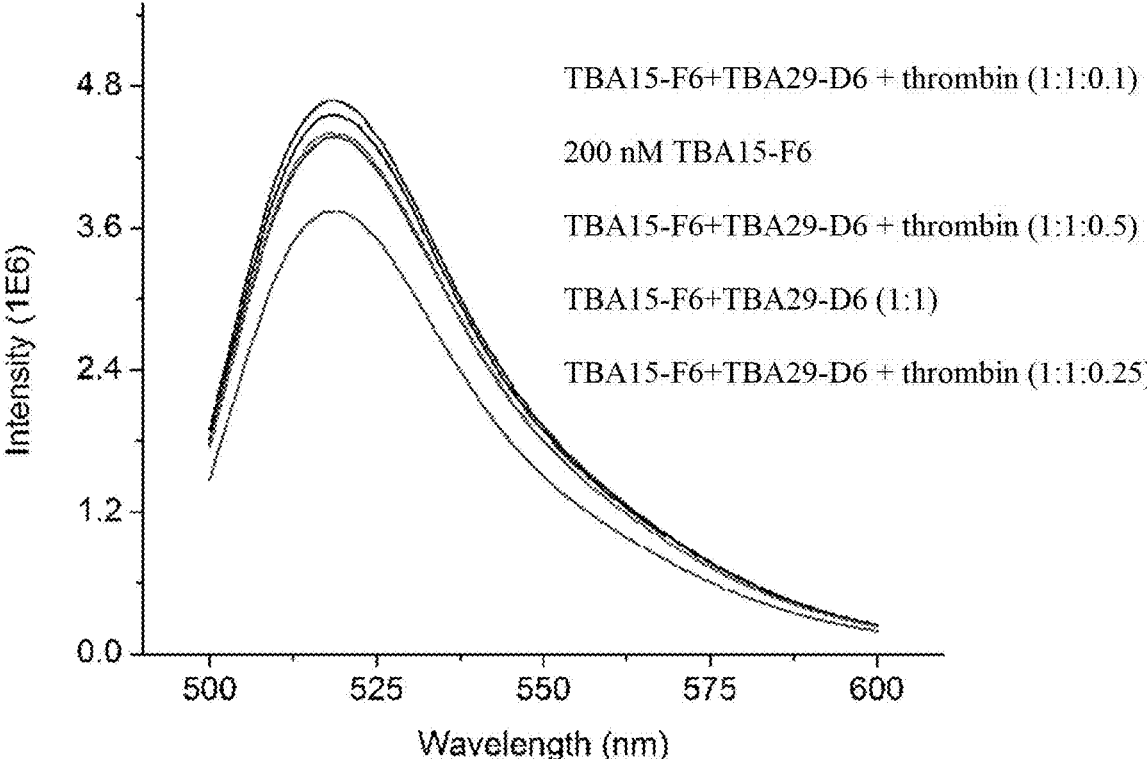
FIG. 7. Graph illustrating fluorescence intensity at varying wavelengths for increasing ratio of thrombin to signaling aptamers TBA15-F6 and TBA29-D6. TBA15-F6 and TBA29-D6 were used as a concentration of 200 nM. Thrombin was used at 20 nM to 100 nM. Complexes in the figure legend are in order of maximum intensity (highest to lowest maximum intensity).

For aptamers TBA15-F6 and TBA29-D6, no specific trend was observed for the different concentrations of thrombin (FIG. 7). No specific trend was observed for the different concentrations of thrombin. The data suggest the two aptamers didn't bind to the thrombin and/or the hybridization sequences of the two signaling aptamers failed to form a duplex.

Figure 8:
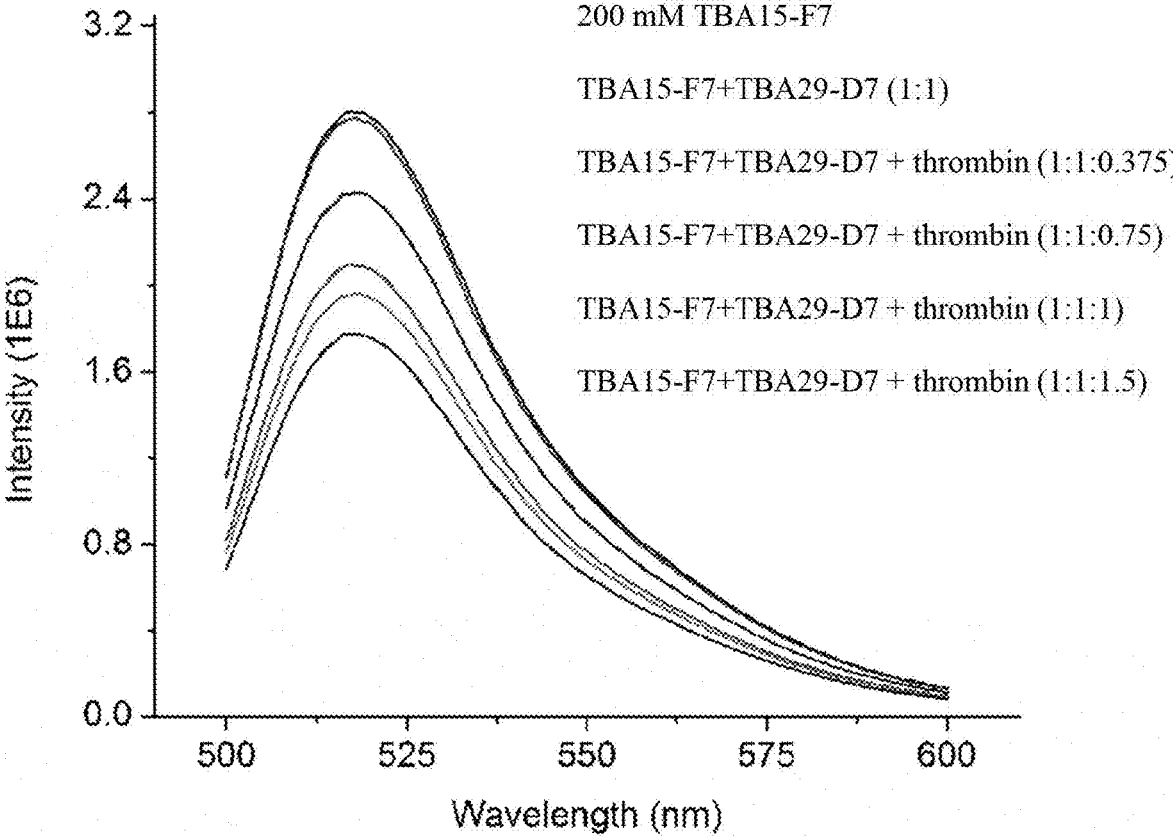
FIG. 8. Graph illustrating fluorescence intensity at varying wavelengths for increasing ratio of thrombin to signaling aptamers TBA15-F7 and TBA29-D7. TBA15-D7 and TBA29-D7 were used as a concentration of 200 nM. Thrombin was used at 75 nM to 300 nM. Complexes in the figure legend are in order of maximum intensity (highest to lowest maximum intensity).

For aptamers TBA15-F7 and TBA29-D7, fluorescence intensity decreased and thrombin concentration increased (FIG. 8). Peak fluorescence intensity for TBA15-D7 alone was $2.806 \times 10^6$, normalized at 100%, and set as $I_{70}$. Peak fluorescence intensity for TBA15-F7+TBA29-D7 (1:1) was $2.768 \times 10^6$, set as $I_{FD7}$. Peak fluorescence intensity of TBA15-F7+TBA29-D7+thrombin (1:1:1) was $1.95 \times 10^6$, set as $I_{FDTHR7}$. $I_{FD7}/I_{70}$ was =98.64%. $I_{FDTHR7}/I_{70}$=69.49%. The data indicate the two signaling aptamers bound to the thrombin and the hybridization sequences formed a duplex. The fluorescence of FITC was quenched by the dabcyl. For TBA15-F7+TBA29-D7 in the solution, fluorescence did not appear to be quenched, indicating binding to thrombin was necessary for duplex formation by the hybridization sequences and quenching of fluorescence.

Figure 9:
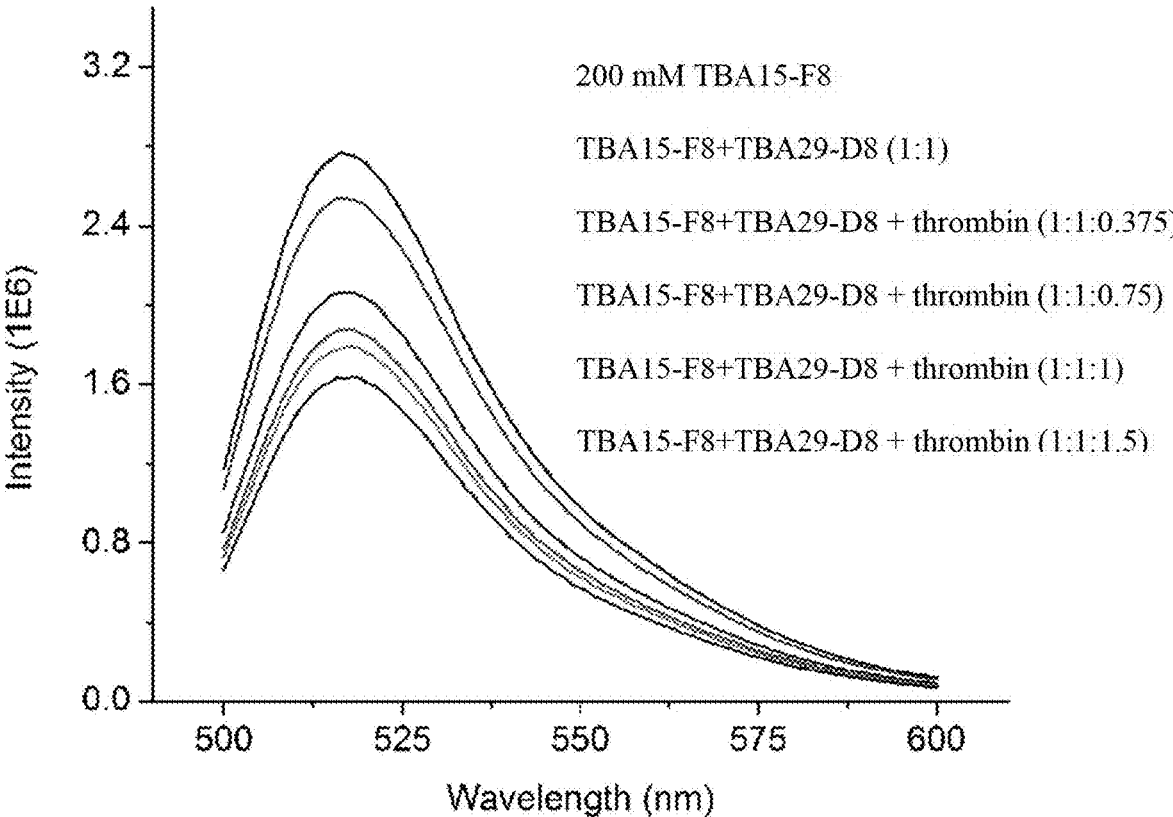
FIG. 9. Graph illustrating fluorescence intensity at varying wavelengths for increasing ratio of thrombin to signaling aptamers TBA15-F8 and TBA29-D8. TBA15-D8 and TBA29-D8 were used as a concentration of 200 nM. Thrombin was used at 75 nM to 300 nM. Complexes in the figure legend are in order of maximum intensity (highest to lowest maximum intensity).

For aptamers TBA15-F8 and TBA29-D8, fluorescence intensity decreased and thrombin concentration increased (FIG. 9). Peak fluorescence intensity for TBA15-D8 alone was $2.76 \times 10^6$, normalized at 100%, and set as $I_{80}$. Peak fluorescence intensity for TBA15-F8+TBA29-D8 (1:1) was $2.54 \times 10^6$, set as $I_{FD8}$. Peak fluorescence intensity of TBA15-F8+TBA29-D8+thrombin (1:1:1) was $1.79 \times 10^6$, set as $I_{FDTHR8}$. $I_{FD8}/I_{80}$ was =92.03%. $I_{FDTHR8}/I_{80}$=64.86%. The data indicate the two signaling aptamers bound to the thrombin and the hybridization sequences formed a duplex. The fluorescence of FITC was quenched by the dabcyl. Compared to the TBA15-F6 and TBA15-F7, improved quenching was observed with TBA15-F8 and TBA29-F8 in the presence of thrombin. A slight decrease in $I_{FD8}/I_{80}$ indicates TBA15-F8 and TBA29-F8 can interact, though weakly, in the absence of thrombin.

Figure 10:
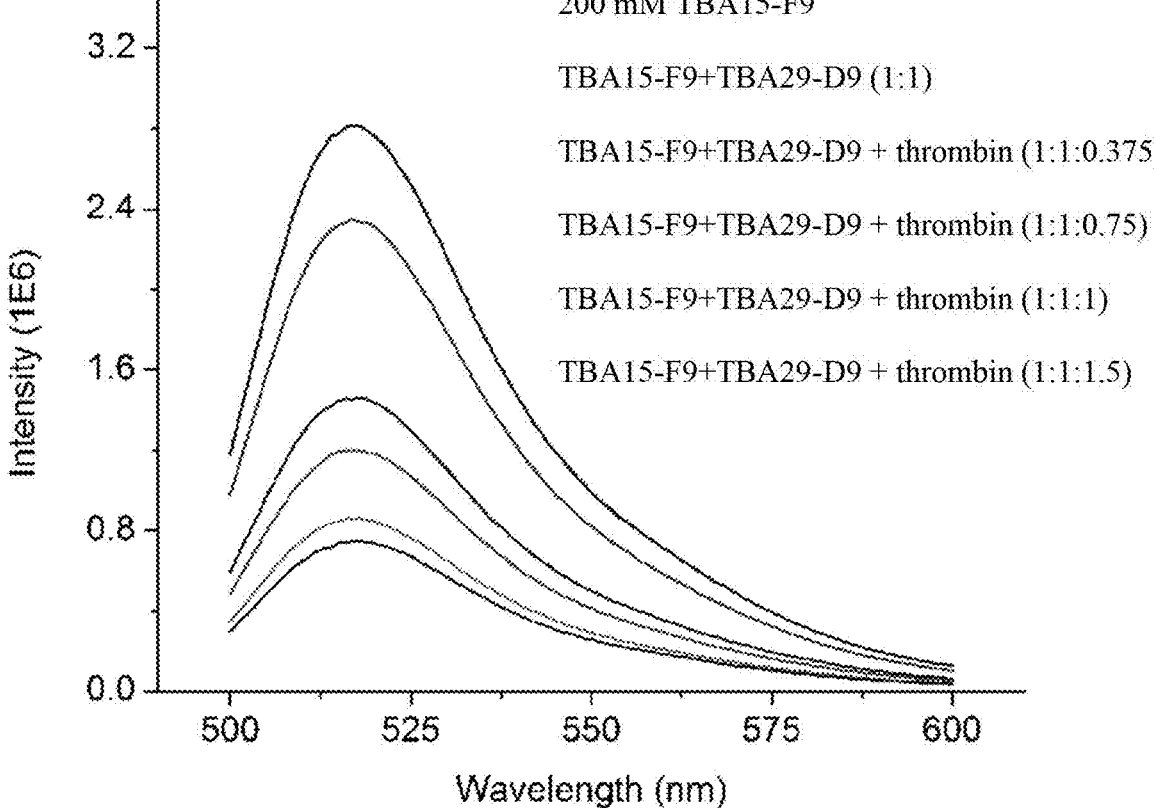
FIG. 10. Graph illustrating fluorescence intensity at varying wavelengths for increasing ratio of thrombin to signaling aptamers TBA15-F9 and TBA29-D9. TBA15-D9 and TBA29-D9 were used as a concentration of 200 nM. Thrombin was used at 75 nM to 300 nM. Complexes in the figure legend are in order of maximum intensity (highest to lowest maximum intensity).

For aptamers TBA15-F9 and TBA29-D9, fluorescence intensity decreased and thrombin concentration increased (FIG. 10). Peak fluorescence intensity for TBA15-D9 alone was $2.81 \times 10^6$, normalized at 100%, and set as $I_{90}$. Peak fluorescence intensity for TBA15-F9+TBA29-D9 (1:1) was $2.35 \times 10^6$, set as $I_{FD9}$. Peak fluorescence intensity of TBA15-F9+TBA29-D9+thrombin (1:1:1) was $0.85 \times 10^6$, set as $I_{FDTHR9}$. $I_{FD9}/I_{90}$ was =83.63%. $I_{FDTHR9}/I_{90}$=30.25%. The data indicate the two signaling aptamers bound to the thrombin and the hybridization sequences formed a duplex. The fluorescence of FITC was quenched by the dabcyl. TBA15-F9 and TBA29-F9 exhibited improved quenching compared to signaling aptamers having 8 base hybridization sequences. As with TBA15-F8 and TBA29-F8, TBA15-F9 and TBA29-F9 showed some quenching in the absence of thrombin.

Figure 11:
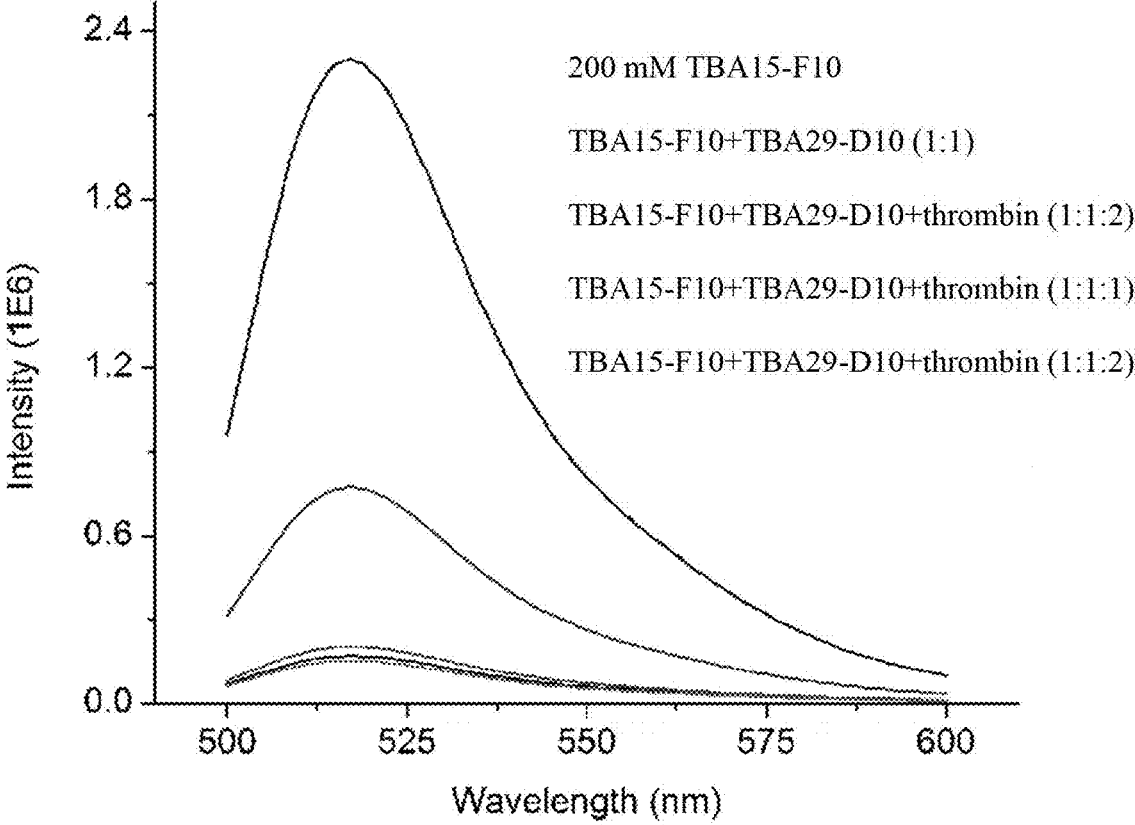
FIG. 11. Graph illustrating fluorescence intensity at varying wavelengths for increasing ratio of thrombin to signaling aptamers TBA15-F10 and TBA29-D10. TBA15-D10 and TBA29-D10 were used as a concentration of 200 nM. Thrombin was used at 75 nM to 300 nM. Complexes in the figure legend are in order of maximum intensity (highest to lowest maximum intensity).

For aptamers TBA15-F10 and TBA29-D10, fluorescence intensity decreased and thrombin concentration increased (FIG. 11). Peak fluorescence intensity for TBA15-D10 alone was $2.30 \times 10^6$, normalized at 100%, and set as $I_{100}$. Peak fluorescence intensity for TBA15-F10+TBA29-D10 (1:1) was $0.775 \times 10^6$, set as $I_{FD10}$. Peak fluorescence intensity of TBA15-F10+TBA29-D10+thrombin (1:1:1) was $0.16 \times 10^6$, set as $I_{FDTHR10}$. $I_{FD10}/I_{100}$ was =33.69%. $I_{FDTHR10}/I_{100}$=6.95%. The data indicate the two signaling aptamers bound to the thrombin and the hybridization sequences formed a duplex. The fluorescence of FITC was quenched by the dabcyl. TBA15-F10 and TBA29-F10 exhibited greater quenching compared to signaling aptamers having 9 base hybridization sequences. TBA15-F10 and TBA29-F10 also exhibited significant quenching in the absence of thrombin.

Based on the results, TBA15-F9+TBA29-D9 was used for additional experimentation.

Example 5. Heparin Selectivity

Figure 14:
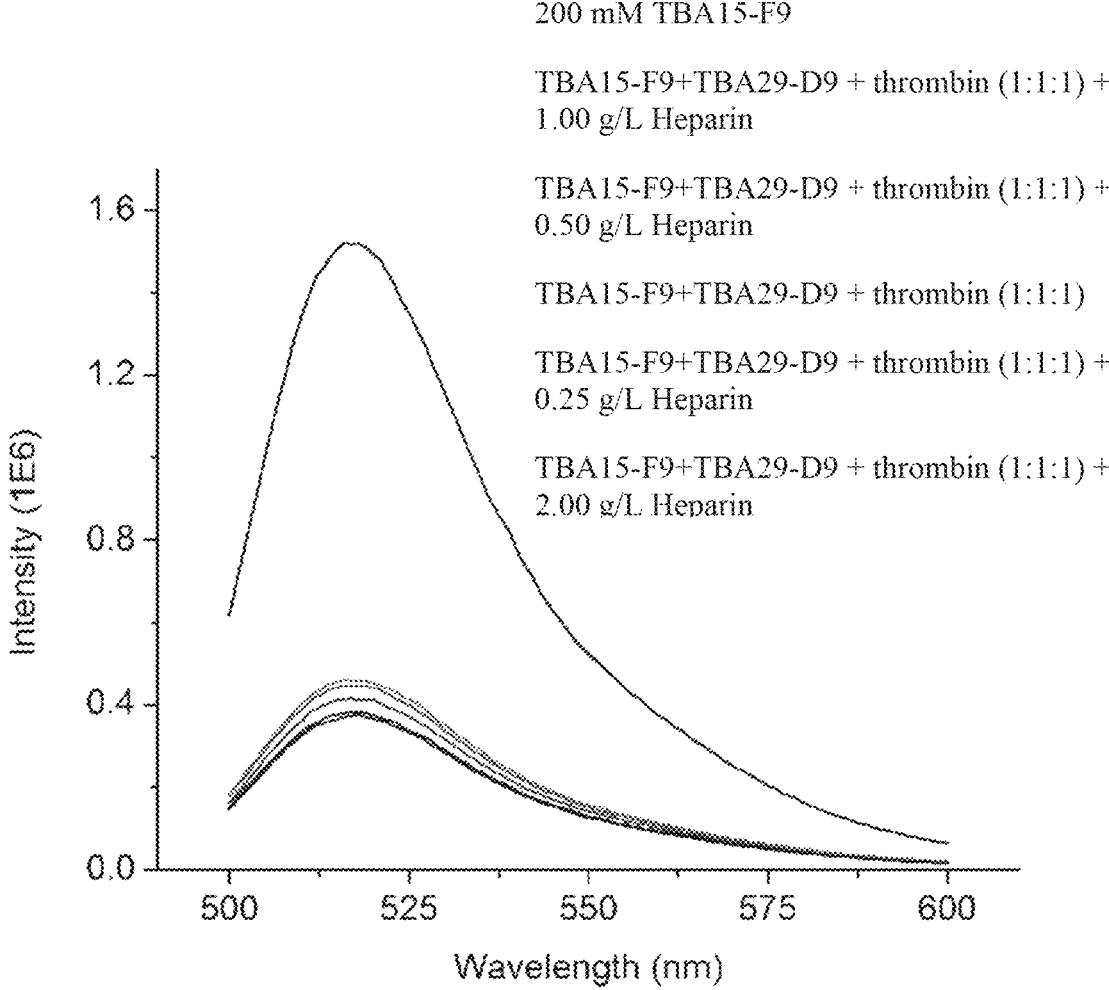
FIG. 14. Graph illustrating fluorescence titration of 200 nM complex with increasing concentration, 0.25 g/L to 2.00 g/L, of heparin. Complexes in the figure legend are in order of maximum intensity (highest to lowest maximum intensity).
Figure 17:
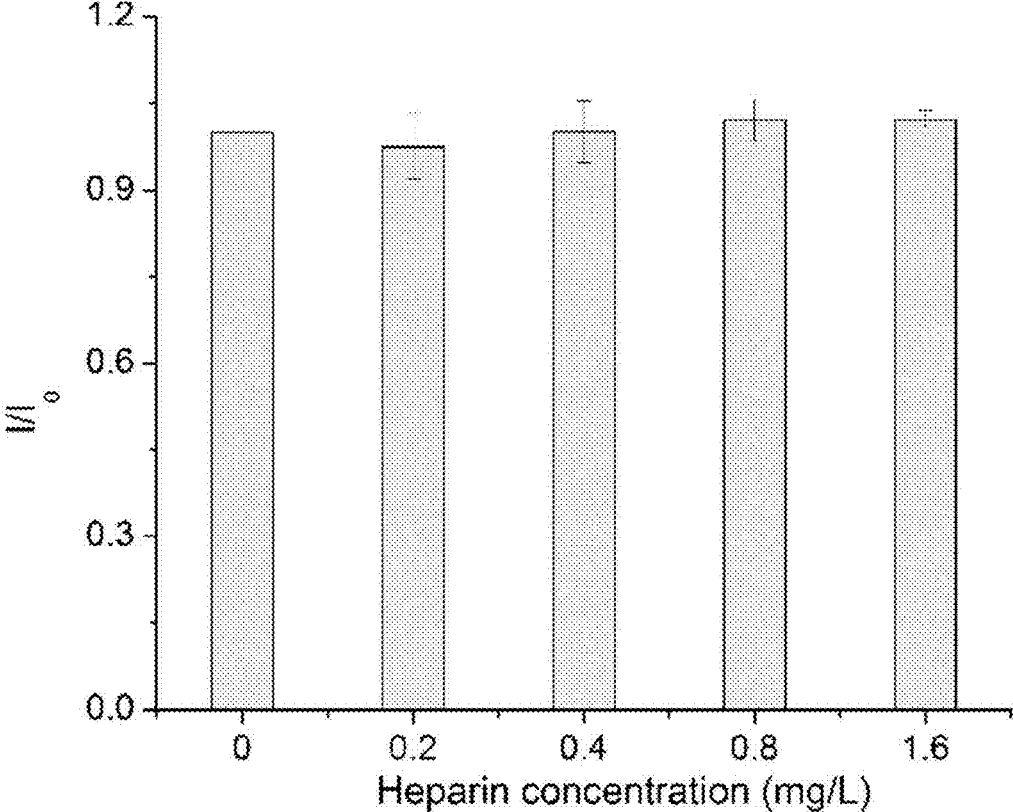
FIG. 17. Graph illustrating fluorescence titration of 200 nM thrombin-signaling aptamer complex with increasing concentration of heparin and ATIII.

The ability of the thrombin-signaling aptamer complexes to accurately detect ATIII in the presence of heparin and human serum protein was tested. 200 nM TBA15-F9 only or 200 nM TBA1.5-F9+TBA29-D9+Thrombin (1:1:1) were used as controls. After complex formation, increasing concentrations of heparin (0.25 g/L to 2.00 g/L) were added and incubated for 30 min at room temperature. The normal concentration of heparin in human plasma is 1.5-3.0 g/L. 1940 nM ATIII was then added and fluorescence spectroscopy was used to for detection. Fluorescence intensity with 1940 nM ATIII alone was normalized to 100%. Fluorescence intensity was not affected by the presence of heparin (FIGS. 14 and 17). The data indicate the thrombin-signaling aptamer complex does not react with heparin. and that the presence of heparin did not adversely affect ATIII detection.

Example 6. Heparin Binding Antigen (HBA) Selectivity

Figure 15:
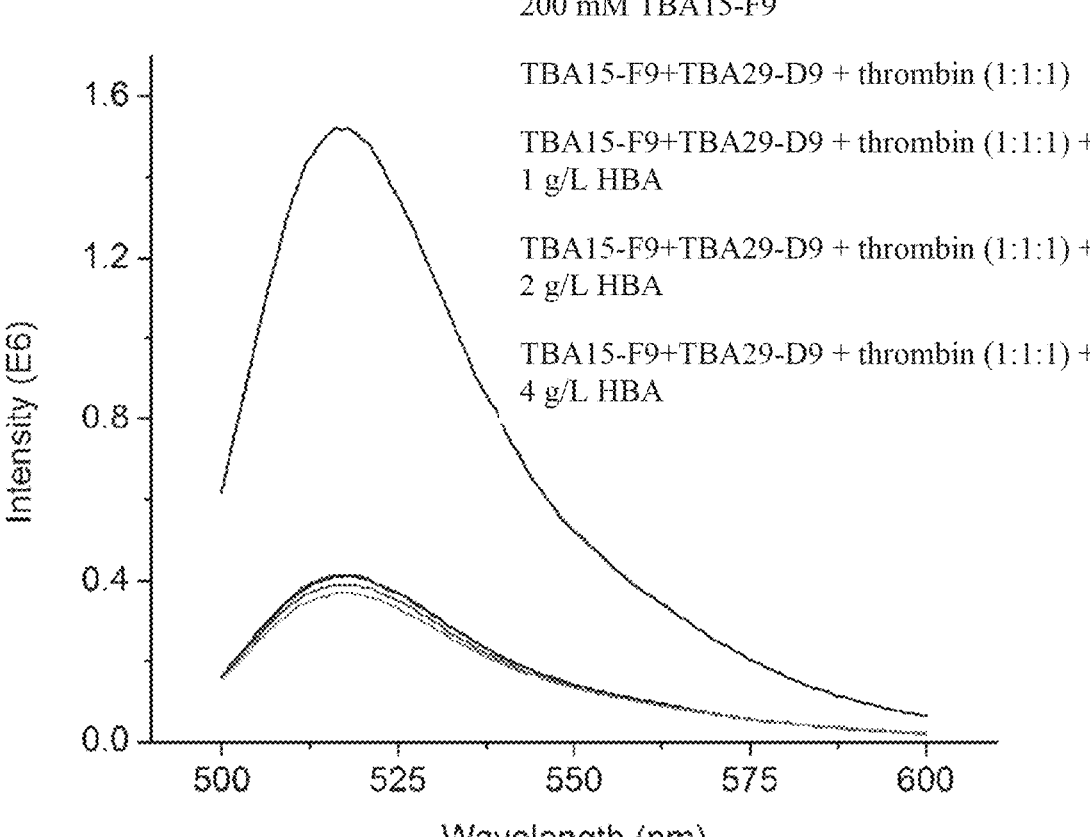
FIG. 15. Graph illustrating fluorescence titration of 200 nM complex with increasing concentration, 1 g/L to 4 g/L, of HBA. Complexes in the figure legend are in order of maximum intensity (highest to lowest maximum intensity).

Similarly to heparin, the ATIII assay was also analyzed for HBA sensitivity. HBA is a protein created by certain bacteria that can interfere with heparin activity and heparin assays. 200 nM TBA15-F9, TBA29-D9 and thrombin (1:1:1) were incubated at room temperature for 30 min to form the thrombin-signaling aptamer complex. Various concentration of HBA were then added to the complexes and incubated for 30 min at room temperature. ATIII was then added to the reactions and detected by fluorescence spectroscopy. Fluorescence intensity was not affected by the presence of heparin biding antigen, indicating the thrombin-signaling aptamer complex does not react with heparin and the presence of HBA does not adversely affect ATIII detection (FIG. 15).

Figure 16:
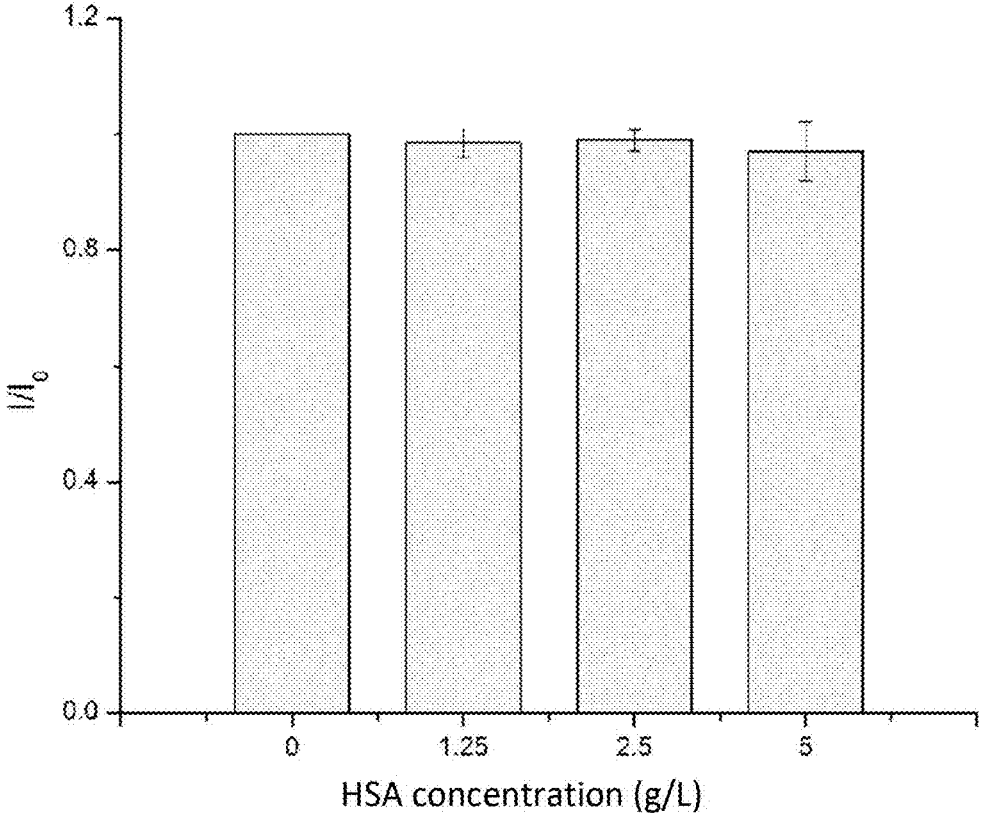
FIG. 16. Graph illustrating fluorescence titration of 200 nM thrombin-signaling aptamer complex with increasing concentration of Human Serum Albumin (HSA) and ATIII.

Similarly, the ATIII assay was also analyzed for human serum albumin sensitivity. Albumin is the most ubiquitous protein circulating in plasma and affects surface activity of the glycocalyx on endothelial cells. Albumin interacts with glucose-aminoglycans, specifically heparin. Sensitivity to HSA was tested in the same manner as sensitivity to HBA. After complex formation, 1940 nM ATIII and increasing concentrations of HSA were added. Fluorescence intensity with 1940 nM ATIII alone was normalized to 100%. HSA presence did not affect fluorescence intensity, indicating HBA does not adversely affect the reaction and the presence of HSA does not adversely affect ATIII detection (FIG. 16).

Example 7. Antithrombin Response Curve

Figure 2:
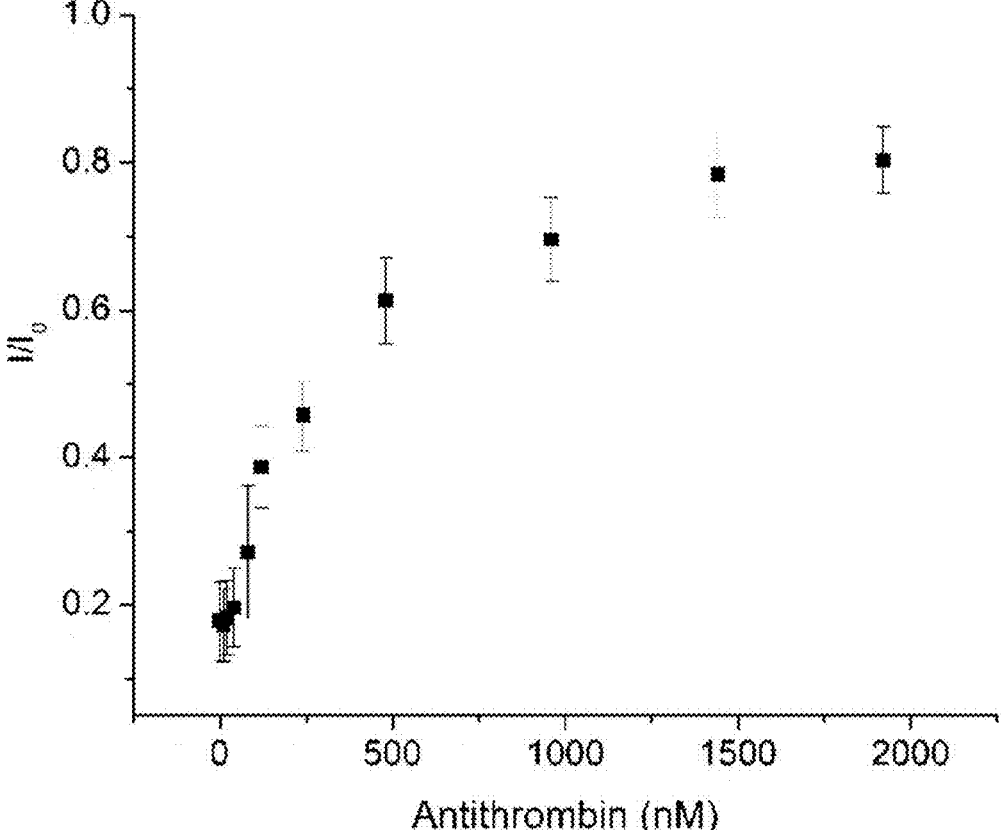
FIG. 2. Graph illustrating a fluorescence increase with increasing concentration of ATIII. Complexes in the figure legend are in order of maximum intensity (highest to lowest maximum intensity).

Varying concentration of ATIII were used to examine the utility of the thrombin-signaling aptamer complexes in quantifying ATIII. Increasing concentrations of ATIII were added to thrombin-signaling aptamer complex and fluorescence detected by fluorescence spectroscopy. There are 3 replicates for each sample (FIG. 2).

The antithrombin was titrated into the TBA15-F9–TBA29-D9–Thrombin complex. The complex concentration was 200 nM. The ratio of TBA15-F9:TBA29-D9:Thrombin was 1:1:1. The antithrombin concentration increased from 10 nM to 1960 nM. Fluorescence intensity of the TBA15-F9 alone control was normalized as 100% set as $I_0$. $I/I_0$ set in the figure y-axis means the intensity of each sample compared to the intensity of FITC in the solution only. Each concentration was repeated for 3 times. The data show the signaling aptamer complexes can be used to quantify ATIII in a sample.

Example 8. Combination of Antithrombin (ATIII) and Heparin

The ability of heparin to promote the reaction between the antithrombin and heparin was analyzed. 200 nM TBA15-F9, TBA29-D9 and thrombin (1:1:1) were incubated for 30 min at room temperature to form thrombin-signaling aptamer complexes. Increasing concentrations of antithrombin were added to the complexes and incubated at room temperature for 30 min and fluorescence detected by fluorescence spectroscopy. There were 3 replicates for each sample.

Example 9. Dynamic Study

Figure 12:
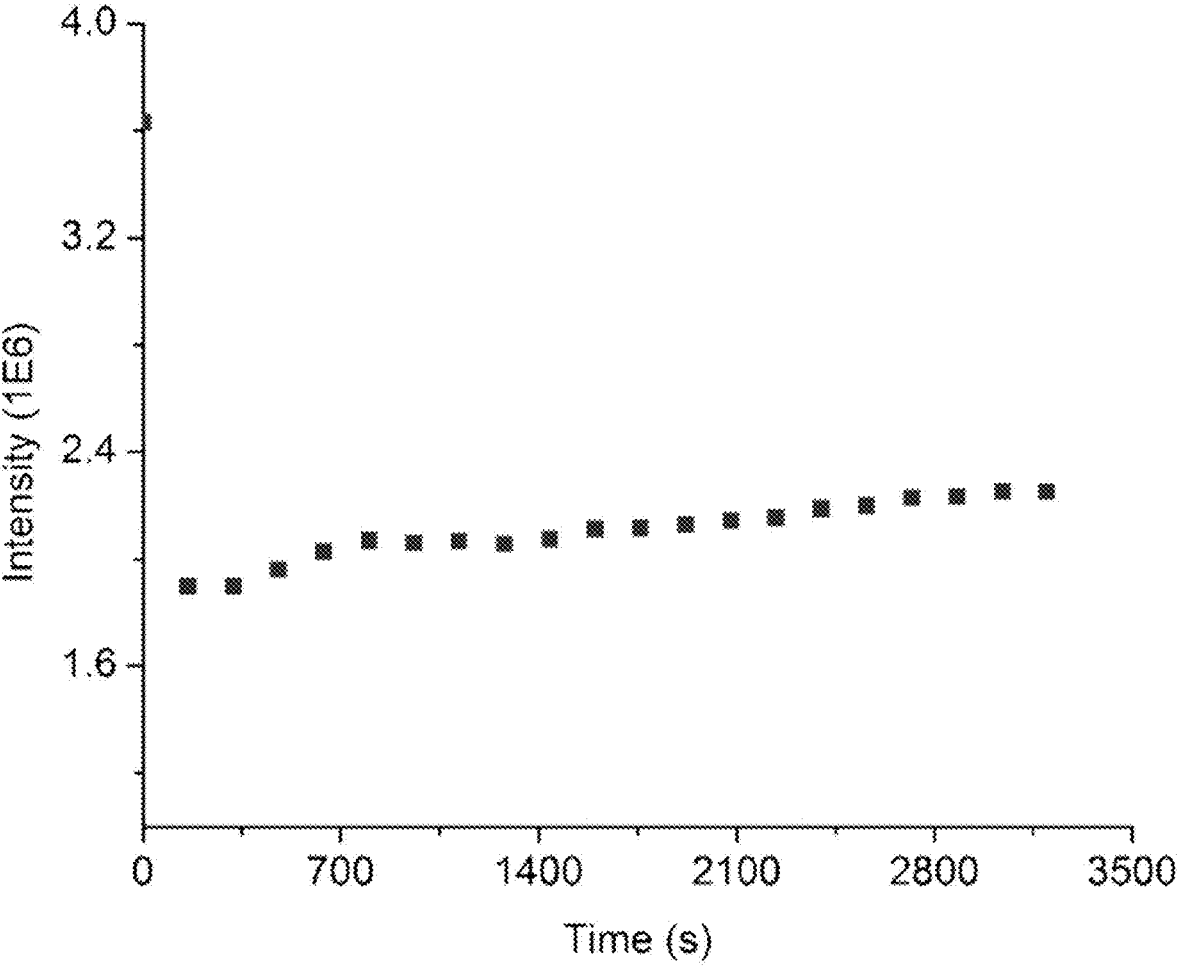
FIG. 12. Graph illustrating kinetics of formation of TBA15-F9+TBA29-D9+thrombin (1:1:1) complexes at 200 nM for each component.

A. TBA15-F9+TBA29-D9+Thrombin dynamics. The 10 μL of 2 μM TBA15-F9 and 10 μL of 2 μM, thrombin were prepared and combined in 78 μL Tris-HCl. 10 μL of 2 μM TBA29-D9 was added to the solution while monitoring fluorescence. The reaction was complete in about 160 seconds (FIG. 12).

B. Complex+Antithrombin Dynamics

Figure 13:
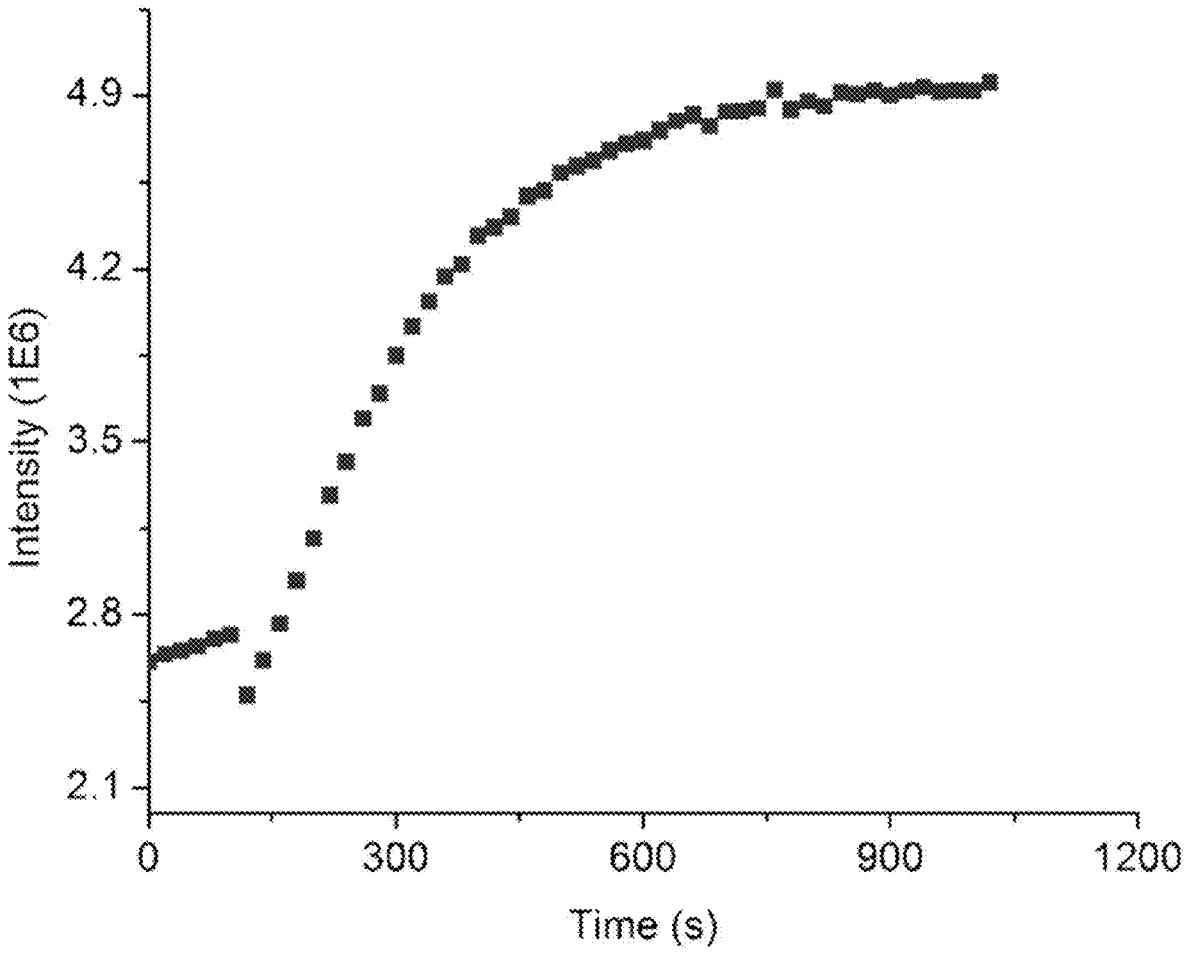
FIG. 13. Graph illustrating kinetics of dissociation of TBA15-F9+TBA29-D9+thrombin (1:1:1) complex in the presence of 1940 nM ATIII. The complex was present at a concentration of 200 nM.

The 12 μL of 2 μM TBA15-F9, 12 μL of 2 μM, TBA29-D9 and 12 μL of 2 μM thrombin were combined in 76 μL Tris-HCl for 30 min at room temperature. 8 μL of 28.47 μM ATIII was then titrated into the solution while monitoring fluorescence. The reaction was complete in about 600 seconds (FIG. 13).

---

The invention claimed is:

1. A kit for determining the level of anti-thrombin (ATIII) in a subject, comprising:
   (a) a first signaling aptamer comprising a first thrombin-specific aptamer comprising the nucleotide sequence of SEQ ID NO:1, a first hybridization sequence, and a fluorescent label; and
   (b) a second signaling aptamer comprising a second thrombin-specific aptamer comprising the nucleotide sequence of SEQ ID NO:2, a second hybridization sequence, and a quencher,
   wherein the first and second hybridization sequences are complementary to each other, and wherein fluorescence of the fluorescent label is quenched when the first and second thrombin-specific signaling aptamers are bound to thrombin.

2. The kit of claim 1, wherein the first and second hybridization sequences are 6-10 nucleobases in length.

3. The kit of claim 2, wherein the first and second hybridization sequences are 9 nucleobases in length.

4. The kit of claim 2, wherein the first hybridization sequence comprises the sequence 5'-GTCGTA-3' and the second hybridization sequence comprises 5'-TACGAC-3' or the first hybridization sequence comprise the sequence 5'-TACGAC-3' and the second hybridization sequence comprises 5'-GTCGTA-3'.

5. The kit of claim 4, wherein the first hybridization sequence comprises the sequence 5'-GTCGTAAGT-3' and the second hybridization sequences comprises the sequence 5'-ACTTACGAC-3' or the first hybridization sequence comprises the sequence 5'-ACTTACGAC-3' and the second hybridization sequences comprises the sequence 5'-GTCGTAAGT-3'.

6. The kit of claim 5, wherein the first and/or second signaling aptamers comprises a linker, wherein the linker connects the thrombin-specific aptamer to the hybridization sequence.

7. The kit of claim 6, wherein the linker comprises polyethylene glycol (PEG).

8. The kit of claim 7, wherein the PEG is $PEG_6$.

9. The kit of claim 8, wherein the fluorescent label comprises FITC, fluorescein, hexochlorofluorescein, rhodamine, Carboxy-X-Rhodamine, tetramethylrhodamine, IAEDANS, EDANS, coumarin, BODIPY FL, lucifer yellow, eosine, erythrosine, Texas Red, or cyanine.

10. The kit of claim 9, wherein the quencher comprises a DABCYL, a BLACK HOLE QUENCHER, or a TAMRA compound.

11. The kit of claim 10, further comprising thrombin.

12. The kit of claim 11, wherein the thrombin, first signaling aptamer, and second signaling aptamer form a complex.

13. A complex comprising: a thrombin; a first signaling aptamer comprising a first thrombin-specific aptamer comprising the nucleotide sequence of SEQ ID NO: 1, a first hybridization sequence, and a fluorescent label; and a second signaling aptamer comprising a second thrombin-specific aptamer comprising the nucleotide sequence of SEQ ID NO: 2, a second hybridization sequence, and a quencher, wherein the first and second hybridization sequences are complementary to each other and form a duplex, and wherein fluorescence of the fluorescent label is quenched.

14. The complex of claim 13, wherein the complex is in a solution, a lyophilized powder or cake, or provided on a test strip.

15. A method of determining the level of ATIII in a sample from a subject, comprising:
   contacting a composition containing the complex of claim 13 with the sample; and
   measuring an increase in fluorescence of the composition,
   wherein the increase in fluorescence is proportional to the level of ATIII in the sample, thereby determining the level of ATIII in the sample.

16. The method of claim 15, wherein the sample comprises a serum sample, a blood sample, or a plasma sample.

17. The method of claim 15, wherein the increase in fluorescence is measured in less than 15 minutes.

18. A method of treating a patient with an anticoagulant comprising:
   (a) determining the level of ATIII in the patient, wherein the determining comprises the steps of:
      (i) contacting a composition containing the complex of claim 15 with a serum, plasma, or blood sample from the patient; and
      ii) measuring an increase in fluorescence of the composition, wherein the increase in fluorescence is proportional to the level of ATIII in the sample thereby determining the level of ATIII in the sample; and
   (b) administering to the patient heparin and/or exogenous ATIII based on the level of ATIII in the sample determined in step (ii).

* * * * *

```
                        SEQUENCE LISTING

<160> NUMBER OF SEQ ID NOS: 22

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
ggttggtgtg gttgg                                                    15

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 2
agtccgtggt agggcaggtt ggggtgact                                     29

<210> SEQ ID NO 3
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 3 gtcgta                                                              6
```

```
<210> SEQ ID NO 4
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 4 tacgac                                                                    6

<210> SEQ ID NO 5
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 5 gtcgtat                                                                   7

<210> SEQ ID NO 6
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 6 atacgac                                                                   7

<210> SEQ ID NO 7
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 7 gtcgtagt                                                                  8

<210> SEQ ID NO 8
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 8 actacgac                                                                  8

<210> SEQ ID NO 9
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 9 gtcgtaagt                                                                 9

<210> SEQ ID NO 10
<211> LENGTH: 9
<212> TYPE: DNA
<213> ORGANISM: Artificial Sequence
<220> FEATURE:
```

-continued

```
<223> OTHER INFORMATION: Synthetic oligonucleotide

<400> SEQUENCE: 10 acttacgac                                                          9

<210> SEQ ID NO 11
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 11
gtcgtaagct                                                         10

<210> SEQ ID NO 12
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 12
agcttacgac                                                         10

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
ggttggtgtg gttgggtcgt a                                            21

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
tacgacagtc cgtggtaggg caggttgggg tgact                             35

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
ggttggtgtg gttgggtcgt at                                           22

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 16
atacgacagt ccgtggtagg gcaggttggg gtgact                            36
```

-continued

```
<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
ggttggtgtg gttgggtcgt agt                                              23

<210> SEQ ID NO 18
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 18
actacgacag tccgtggtag ggcaggttgg ggtgact                              37

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
ggttggtgtg gttgggtcgt aagt                                             24

<210> SEQ ID NO 20
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 20
acttacgaca gtccgtggta gggcaggttg gggtgact                             38

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21
ggttggtgtg gttgggtcgt aagct                                            25

<210> SEQ ID NO 22
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 22
agcttacgac agtccgtggt agggcaggtt ggggtgact                            39
```